(12) United States Patent
Balloul et al.

(10) Patent No.: US 8,778,675 B2
(45) Date of Patent: Jul. 15, 2014

(54) IMMORTALIZED AVIAN CELL LINES AND USE THEREOF

(71) Applicant: Transgene S.A., Illkirch Graffenstaden (FR)

(72) Inventors: Jean-Marc Balloul, Strasbourg (FR); Marina Kapfer, Schiltigheim (FR); Thierry Menguy, Gif S/Yvette (FR)

(73) Assignee: Transgene S.A., Illkirch (FR)

( * ) Notice: Subject to any disclaimer, the term of this patent is extended or adjusted under 35 U.S.C. 154(b) by 17 days.

(21) Appl. No.: 13/775,314

(22) Filed: Feb. 25, 2013

(65) Prior Publication Data

US 2013/0236929 A1     Sep. 12, 2013

Related U.S. Application Data

(62) Division of application No. 12/777,731, filed on May 11, 2010, now Pat. No. 8,445,270.

(60) Provisional application No. 61/213,484, filed on Jun. 12, 2009.

(30) Foreign Application Priority Data

May 12, 2009 (EP) ..................................... 09305422

(51) Int. Cl.
*C12N 5/00* (2006.01)
*C12N 15/00* (2006.01)

(52) U.S. Cl.
USPC .......................................... 435/325; 435/455

(58) Field of Classification Search
USPC ................................................ 435/325, 455
See application file for complete search history.

(56) References Cited

U.S. PATENT DOCUMENTS 5,672,485 A * 9/1997 Foster et al. ............... 435/40.51

FOREIGN PATENT DOCUMENTS

EP    WO 2007/077256 A1 *  7/2007
WO    WO 2007/077256 A1    7/2007

OTHER PUBLICATIONS

Freire (Vaccine, 2005, vol. 23, p. 2501-2512).*
Camacho et al., *Immunogenicity of WHO-17D and Brazilian 17DD yellow fever vaccines: a randomized trial*, 38(5) Rev. Saude Publica 671-678 (2004).
Delaney et al., *The chicken telomerase reverse transcriptase (chTERT): molecular and cytogenetic characterization with a comparative analysis*, 339 Gene 61-69 (2004).
Fallaux et al., *New helper cells and matched early region 1-deleted adenovirus vectors prevent generation of replication-competent adenoviruses*, 9 Human Gene Therapy 1909-1917 (1998).
Fragnet et al., *Virus et telomerase*, 9 Virologie 443-455 (2005).
Freire et al. *Production of yellow fever 17DD vaccine virus in primary culture of chicken embryo fibroblasts: yields, thermo and genetic stability, attenuation and immunogenicity*, 23 Vaccine 2501-2512 (2005).
Greenberg et al., *Expression of mouse telomerase reverse transcriptase during development, differentiation and proliferation*, 16 Oncogene 1723-1730 (1998).
Mateau et al, *Construction and biological properties of yellow fever 17D/dengue type 1 recombinant virus*, 101 Transcription of the Royal Society of Tropical Medicine and Hygiene 289-298 (2007).
McSharry et al., *Human telomerase reverse transcriptase-immortalized MRC-5 and HCA2 human fibroblasts are fully permissive for human cytomegalovirus*, 82 Journal of General Virology 855-863 (2001).
Michailidis et al., *Endogenous and ectopic expression of telomere regulating genes in chicken embryonic fibroblasts*, 335 Biochemical and Biophysical Research Communications 240-246 (2005).
Monath et al., *Safety testing for neurovirulence of novel live, attenuated flavivirus vaccines: Infant mice provide an accurate surrogate for the test in monkeys*, 33 Biologicals 131-144 (2005).
Nakamura et al., Telomerase catalytic subunit homologs from fission yeast and human, 277 Science 955-960 (1997).
Pau et al., *The human cell line PER.C6 provides a new manufacturing system for the production of influenza vaccines*, 19 Vaccine 2716-2721 (2001).
Santos et al., *Complete nucleotide sequence of yellow fever virus vaccine strains 17DD and 17D-213*, 35 Virus Research 35-41 (1995).
Toriniwa et al., Long term stability of Vero cell-derived inactivated Japanese encephalitis vaccine prepared using serum-free medium, 26 Vaccine 3680-3689 (2008).
Yallop et al., *High level production of recombinant IGG in the human cell line per C6*, Animal Cell Technology Meet Genomics 533-536 (2005).

* cited by examiner

*Primary Examiner* — Michael C. Wilson
(74) *Attorney, Agent, or Firm* — Buchanan Ingersoll & Rooney PC

(57) ABSTRACT

The present invention relates to specific immortalized avian cell lines expressing telomerase reverse transcriptase (TERT), and exhibiting distinct biologics production patterns. More particularly, the present invention relates to immortalized avian cell line capable of either amplifying Flaviviridae but not capable of amplifying Vaccinia virus strain Copenhagen (VV-COP) nor Modified Vaccinia virus Ankara (MVA), or capable of amplifying both Flaviviridae and Poxviridae. The invention further relates to the use of said immortalized avian cell lines and related methods for producing biologics, including viruses and proteins.

8 Claims, 14 Drawing Sheets

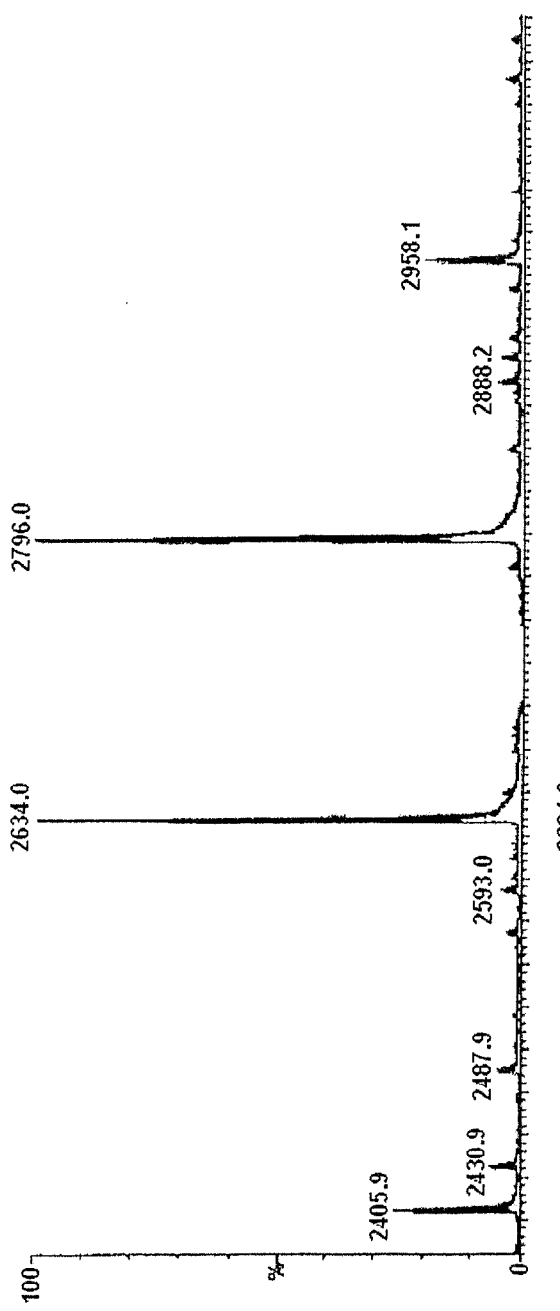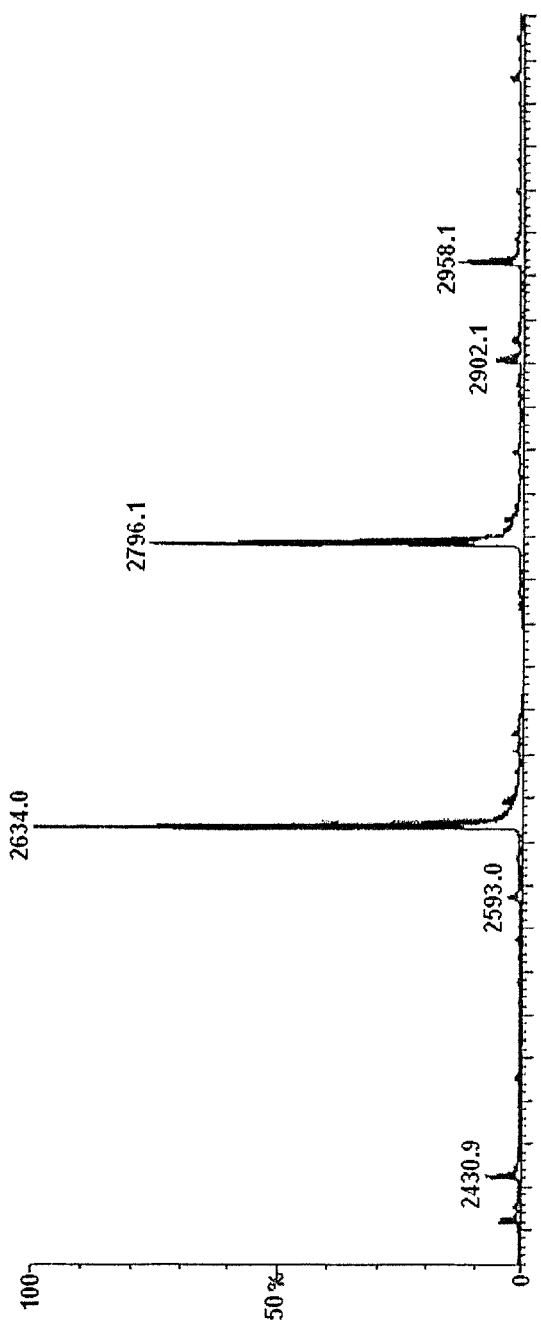

IMMORTALIZED AVIAN CELL LINES AND USE THEREOF

CROSS REFERENCE TO RELATED APPLICATIONS

This application is a Divisional Application of U.S. patent application Ser. No. 12/777,731, filed on May 11, 2010, which claims priority under 35 U.S.C. §119 to U.S. Provisional Patent Application 61/213,484, filed on Jun. 12, 2009, and EP 09305422.9, filed on May 12, 2009; the content of each is hereby expressly incorporated by reference in their entireties for all purposes and each is assigned to the assignee hereof.

TECHNICAL FIELD

The present invention pertains to the field of cell lines for the production of biologics, including viruses and proteins. In particular, the invention relates to specific immortalized avian cell lines expressing telomerase reverse transcriptase (TERT), and exhibiting distinct biologics production patterns. More particularly, the present invention relates to immortalized avian cell line capable of either amplifying Flaviviridae but not capable of amplifying Vaccinia virus strain Copenhagen (VV-COP) nor Modified Vaccinia virus Ankara (MVA), or capable of amplifying both Flaviviridae and Poxviridae. The invention further relates to the use of said immortalized avian cell lines and related methods for producing biologics, including viruses and proteins.

BACKGROUND OF THE INVENTION

Avian cells have been used for years for the production of viral vaccines. For instance, embryonated chick eggs are able to support the replication of a wide range of human and animal viruses including notably attenuated viruses which have impaired potential to replicate in human or mammalian cells. Embryonated chick eggs used for human viral vaccine production must be certified to be free of a defined set of viral and bacterial contamination (specific pathogen-free or SPF). Embryonated chick eggs are expensive and can constitute up to 40% of the cost of viral vaccines. A vaccine lot cannot be released until the SPF supplier verifies that the parental chickens for the embryonated chick eggs used to manufacture the vaccine lot were completely free of any disease. This uncertainty adds a significant cost to the preparation of these vaccines. In addition, the large-scale processes for infecting eggs and maintaining virus growth are time consuming and sometimes inconsistent across different vaccine batches.

With the development of cell culture techniques vaccine manufacturers have replaced embryonated chick eggs with isolated chicken embryo fibroblasts (CEFs). Most Flaviviridae vaccines are for instance manufactured from CEFs. The Flaviviridae Yellow fever viral vaccines recommended by the World Health Organization (WHO) are from 17D strain and substrains, which have minor differences in nucleotide sequences and equivalent immunogenicity (CAMACHO L. A. B. et al., *Rev Saude Publica* 38(5):671-8 (2004); DOS SANTOS C. N., *Virus Res.* 35:35-41 (1995)). Experiments regarding Flaviviridae viral production process have resulted in the establishment of an efficient methodology for the production of a Yellow fever viral vaccine in CEFs using the 17DD virus strain (FREIRE M. S., *Vaccine* 23, 2501-2512 (2005)). While the use of CEFs improves the safety profile, efficiency and reliability of the manufacturing process, it also highly time consuming and further increases costs. The production of CEFs depends indeed on the availability of SPF eggs. The CEFs are prepared from SPF eggs by mincing embryos to establish and amplify viable cells. Typical for primary animal cells the fibroblasts suffer senescence: the doubling time increases with passaging and eventually all cells die. This process occurs after about 20 passages. This limited live span constraints to perform a complete set of safety tests for each lot of CEFs.

Due to the limitations of embryonated chicken eggs and CEFs as previously described for manufacturing viral vaccines, the search for new cell culture systems have drawn considerable attention over the past decades. In this respect immortalized cell lines are highly attractive. Immortalized cell lines can be maintained or frozen from batch to batch on the production site and are always available for a new production process. Moreover as they are confined at the production plant, they are less subject to contamination by exogenous contaminant. Their use allows a drastic reduction of the manual manipulation needed for the production process. All these properties lead to a reduction of the price and of the duration of the production process as well as a diminution of the potential contamination. Immortalized cell lines can moreover be fully characterized and are thus totally compliant with the good laboratory practice and the requirements of the different medical agencies. As an example, VERO cell line has been described as alternative candidate for Flaviviridae vaccine production in replacement of the approved embryonated chicken eggs. The live attenuated Japanese encephalitis virus vaccine ChimeriVax™-JEV was propagated in VERO cells cultured in media supplemented with fetal bovine serum (MONATH et al., *Biologicals,* 33:131-144 (2005)). Similarly, MATEU et al. (*Trans. R. Soc. Trap. Med. Hyg.,* 101(3):289-98 (2007)) and TORINIWA et al. (*Vaccine,* 4; 26(29-30):3680-9 (2008)) have respectively produced Yellow fever virus vaccine and Japanese encephalitis virus vaccine in VERO cell line. The application of immortalized cell lines is moreover not limited to the viral vaccines they are designed for but may be extended to recombinant proteins. For example, both antibodies and influenza viral vaccines can be propagated on PER.C6® cell line (ECACC number 96022940), a human fetal retinoblast cell line immortalized by transfection with an E1 minigene of adeno virus type 5. (FALLAUX F. J. et al., *Hum. Gene Ther.* 9:1909-17 (1998); PAU M. G. et al., *Vaccine* 19, 2716-2721 (2001); YALLOP C. et al., *Animal Cell Technology meets Genomics,* 533-536 (2005)).

However alternative immortalized cell lines are still needed. WO2007/077256 provides methods for immortalizing primary avian cells by transfection with the *Cairina moschata* telomerase reverse transcriptase (TERT) nucleic acid molecule either by targeted or random insertion of the TERT nucleic acid molecule into the *Cairina moschata* primary avian cells genome. Based on said methods, especially by random insertion, we have now identified new immortalized avian cell lines which have distinguished properties from one another.

DISCLOSURE OF THE INVENTION

As used throughout the entire application, “a” and “an” are used in the sense that they mean “at least one”, “at least a first”, “one or more” or “a plurality” of the referenced components or steps, unless the context clearly dictates otherwise.

As used throughout the entire application, “and/or” wherever used herein includes the meaning of “and”, “or” and “all or any other combination of the elements connected by said term”.

As used throughout the entire application, "comprising" and "comprise" are intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used throughout the entire application, "about" or "approximately" as used herein means within 20%, preferably within 10%, and more preferably within 5% of a given value or range.

As used throughout the entire application, an "immortalized avian cell line" refers to an avian cell line that proliferates in culture beyond the Hayflick limit (HAYFLICK L., *Clin. Geriatr. Med.* 1(1):15-27 (1985)). More particularly, an "immortalized avian cell line" refers to an avian cell line that is capable of growing in culture for greater than 30 passages that maintain a doubling time in culture of about 1 to about 2 days and have been in continuous culture for greater than about 6 months. An avian cell line is considered immortalized after about 20 to about 25 passages in culture. Immortalized avian cells are differentiated from transformed cells in that unlike transformed cells, immortalized avian cells are growth arrested (i.e. avian cells are confluent and subject to contact inhibition) and have a homogenous fibroblast like morphology.

As used throughout the entire application, the terms an "immortalized avian cell line able of amplifying a virus" mean that an immortalized avian cell line of the invention is able after infection by a virus to increase the amount of said virus due to a productive viral replication of the virus in the infected cells. The term "reproductive replication" refers to the fact that the said virus replicates in the immortalized avian cell line to such an extent that infectious progeny virus is produced, wherein the ratio of output virus to input virus is above 1. In other words, "able of amplifying a virus" means that the ratio of output virus to input virus should be above 1.

As used throughout in the entire application, "Flaviviridae" include Flaviviruses, Pestiviruses, Hepaciviruses, GB virus A, GB virus A-like agents, GB virus-B and GB virus-C (also called hepatitis G virus). Classification, genome organisation and replication cycle of Flaviviridae has been well described (LINDENBACH B. D. at al., in D. M. Knipe and P. M. Howley, Fields Virology 5$^{th}$ Edition, Eds. Lippincott-Raven Publishers, Philadelphia (2007)).

As used throughout in the entire application, "Flaviviruses" include the "mosquito-borne virus cluster", the "tick-borne virus cluster" and the "no-vector cluster" (KUNO G. et al., *J. Virol.* 72, 73-83 (1998)).

The "mosquito-borne virus cluster" includes Dengue virus, Japanese encephalitis virus, Murray Valley encephalitis virus, St. Louis encephalitis virus, West Nile virus, Yellow fever virus, Kunjin virus, Rocio virus and Ilheus virus.

Dengue virus (DENV) strains are divided into the four serotypes DEN-1, DEN-2, DEN-3 and DEN-4. Information on the nucleotide sequences of the genomes of DENVs can also be obtained from publicly accessible gene databases such as GenBank: DEN-1 virus (e.g. GenBank accession number M23027); DEN-2 virus (e.g. GenBank accession number M19197; NC-001474); DEN-3 virus (e.g. GenBank accession number M93130); DEN-4 virus (e.g. GenBank accession number M14931).

Japanese encephalitis virus (JEV) includes the strains: P3, SA14, S892, GP78, ThCMAr4492, ThCMAr6793, JaGAr01, Jaoars982, Subin, KE-093/83, Nakayama wild-strain, Nakayama-RFVL, Nakayama-Yoken, LNDG07-02, LNDG07-16 and K94P05. Information on the nucleotide sequences of the genomes of JEVs can also be obtained from publicly accessible gene databases such as GenBank: e.g. GenBank accession number AF045551.

West Nile virus (WNV) strains are including genotypes NY99 and WN02. Information on the nucleotide sequences of the genomes of WNVs can also be obtained from publicly accessible gene databases such as GenBank: e.g. GenBank accession number M12294; NC-001563.

The Yellow fever virus (YFV) strains include the strains: Asibi, French viscerotropic virus (FVV), B4.1, Rendu, Dak1279, 17D, 17DD, 17D-204, Colombia 88, F-204 and C-204 (HAHN et al., *Proceedings of the National Academy of Sciences USA* 84, 2019-2023 (1987); WANG et al., *J. of Gen. Virol.* 76, 2749-2755 (1995); BALLINGER-CRABTREE & MILLER, *J. of Gen. Virol.* 71, 2115-2121 (1990)); WANG H. et al., *J. of Gen. Virol.* 78, 1349-1352 (1997); CAMACHO L. A. B. et al., *Rev Saude Publica* 38(5):671-8 (2004); DOS SANTOS C. N., *Virus Res.* 35:35-41 (1995); GALLER R. et al., *Braz. J. Med. Biol. Res.* volume 30(2), 157-168 (1997). The Yellow fever virus (YFV) has been studied at the genetic level (RICE et al., *Science* 229:726-733 (1985)) and information correlating genotype and phenotype has been established (MARCHEVSKY et al., *Am. J. Trop. Med. Hyg.* 52:75-80 (1995)). Information on the nucleotide sequences of the genomes of YFVs can also be obtained from publicly accessible gene databases such as GenBank: e.g. GenBank accession number X03700; NC-002031.

The "tick-borne virus cluster" refers to Tick-borne encephalitis virus (TBEV) (also called Tick-borne meningoencephalitis virus) which includes three subtypes: the Western subtype (also called Central European encephalitis virus), the Far Eastern subtype (also called Russian spring/summer encephalitis virus) and the Siberian subtype (KAISER and REINHARD, *Infectious Disease Clinics of North America.* 22(3):561-575 (2008)). Information on the nucleotide sequences of the genomes of TBEVs can also be obtained from publicly accessible gene databases such as GenBank: e.g. GenBank accession number U27495, NC-001672. TBEV also includes the viable chimeric vaccine was constructed which contained the C-preM-E or preM-E structural protein genes of a virulent Far Eastern Russian TBEV with the remaining nonstructural protein genes and 5'- and 3'-noncoding sequences derived from DEN4 [TBEV (CME)/DEN4 and TBEV(ME)/DEN4, respectively] (PLETNEV et al., *Proc. Natl. Acad. Sci. U.S.A.* 89:10532-10536, (1992)).

The "no-vector cluster" includes Apoi virus, cell fusing agent virus, San Perlita virus, Jutiapa virus, Montana myotis leukoencephalitis virus, Modoc virus, Cowbone Ridge virus, Sal Vieja virus, Bukalasa bat virus, Dakar bat virus, Rio Bravo virus, Carey Island virus, Phnom Penh bat virus and Batu Cave virus (KUNO G. et al., *J. Virol.,* 72 73-83 (1998)). Information on the nucleotide sequences of the genomes of no-vector viruses can also be obtained from publicly accessible gene databases such as GenBank. For instance, for Apoi virus: e.g. GenBank accession number AF160193, NC-003676.

As used throughout in the entire application, "Pestiviruses" include Border disease virus (BDV), Bovine viral diarrhea virus (BVDV) and classical swine fever virus (CSFV). BDV includes the 3 genotypes BDV-1 to -3 (BECKER et al. *Virology* 311 96-104 (2003)). BVDV includes BVDV type 1

(BVDV-1) and BVDV type 2 (BVDV-2) (HEINZ et al. in Seventh Report of the International Committee on Taxonomy of Viruses, 859-868, Edited by M. H. V. Van Regenmortel, C. M. Fauquet, D. H. L. Bishop & 8 other editors. San Diego: Academic Press (2000)).

As used throughout in the entire application, "Hepaciviruses" include hepatitis C virus (HCV). Extensive phylogenetic analyses have led to the classification of HCV isolates into 6 major genotypes (1 to 6) containing different subtypes (a, b, c, etc. . . . ) (SIMMONS et al., Hepatology 42, 962-973 (2005)). Exemplary HCV isolates of genotype 1a include without limitation, HCV-1 (CHOO et al., Proc. Natl. Acad. Sci. USA 88, 2451-2455 (1991)), -J1 (OKAMOTO et al., Nucleic Acids Res. 20, 6410-6410 (1992)) and -H (IN-CHAUSPE et al., Proc. Natl. Acad. Sci. 88, 10292-10296 (1991)). Exemplary HCV isolates of genotype 1b include without limitation, HCV-JA (KATO et al., Proc. Natl. Acad., Sci. 87, 9524-9528 (1990)) and BK (TAKAMIZAWA et al., J. Virol. 65, 1105-1113 (1991)). Exemplary HCV isolates of genotype 1c include without limitation, HCV-G9 (OKAMOTO et al., J. Gen. Viral. 45, 629-635 (1994)). Exemplary HCV isolates of genotype 2a include without limitation, HCV-J6 (OKAMOTO et al., J. Gen. Virol. 72, 2697-2704 (1991)). Exemplary HCV isolates of genotype 2b include without limitation, HCV-J8 (OKAMOTO et al., Virology 188, 331-341 (1992)). Exemplary HCV isolates of genotype 2c include without limitation, HCV-BEBE1 (NAKO et al., J. Gen. Virol. 141, 701-704 (1996)). Exemplary HCV isolates of genotype 3a include without limitation, HCV-NZL1 (SAKAMOTO et al., J. Gen. Virol. 75, 1761-1768 (1994)). Exemplary HCV isolates of genotype 3b include without limitation, HCV-Tr (CHAYAMA et al., J. Gen. Virol. 75, 3623-3628 (1994)). Exemplary HCV isolates of genotype 4a include without limitation, HCV-ED43 (CHAMBERLAIN et al., J. Gen. Viral. 78, 1341-1347 (1997)). Exemplary HCV isolates of genotype 5a include without limitation, HCV-EUH1480 (CHAMBERLAIN et al., Biochem. Biophys. Res. Commun. 236, 44-49 (1997)). Exemplary HCV isolates of genotype 6a include without limitation, HCV-EUHK2 (ADAMS et al., Biochem. Biophys. Res. Commun. 234, 393-396 (1997)).

As used throughout in the entire application, "Poxviridae" include Orthopoxviruses, Capripoxviruses, Avipoxviruses, Parapoxviruses and Leporipoxviruses, and derivatives thereof.

Orthopoxviruses include Buffalopoxvirus, Camelpoxvirus, Cowpoxvirus, Ectromelia virus, Monkeypoxvirus, Rabbitpoxvirus, Variola virus, Vaccinia virus (VV) and its derivatives such as for instance Modified Vaccinia virus Ankara (MVA).

Capripoxviruses include sheeppox virus, goatpox virus and lumpy skin disease virus.

Avipoxviruses include Canarypoxvirus and Fowlpoxvirus.

Parapoxviruses include pseudocowpox, arapoxvirus ovis and orf virus.

Leporipoxviruses include Myxoma virus.

Sequences of the genome of various Poxviridae are available in the art, for example, the VV Western reserve, VV Copenhagen, Modified Vaccinia virus Ankara, Cowpoxvirus, Canarypoxvirus, Ectromelia virus, Myxoma virus genomes are available in Genbank (accession number NC_006998, M35027, U94848, NC_003663, NC_005309, NC_004105, NC_001132 respectively).

As used throughout in the entire application, "Vaccinia virus" (VV) includes the VV strains: Dairen I, IHD-J, L-IPV, LC16M8, LC16MO, Lister, LIVP, Tashkent, WR 65-16, Wyeth, Ankara, Copenhagen (COP) (GOEBEL et al. (1990); Genbank accession number M35027.1), Tian Tan, Western Reserve (WR), Modified Vaccinia virus Ankara (MVA), VV comprising a defective J2R gene (see WEIR and MOSS 1983; Genbank accession number AAA48082), VV comprising a defective F2L gene (see WO2009/065547), W comprising defective I4L and/or F4L gene(s) (see WO2009/065546), and derivatives thereof.

As used throughout in the entire application, "Modified Vaccinia virus Ankara (MVA)" refers to the highly attenuated VV generated by serial passages on CEFs of the VV strain Ankara (MAYR A. et al., Infection 3, 6-14 (1975)) and derivatives thereof. The MVA virus was deposited before Collection Nationale de Cultures de Microorganismes (CNCM) under depositary N° I-721. The MVA is fully described in SUTTER et MOSS (Proc. Natl. Acad. Sci. USA 89, 10847-10851 (1992)). The genome of the MVA has been mapped and sequenced (ANTOINE et al., Virol. 244, 365-396 (1998) and is available in Genbank under accession number U94848).

According to a first embodiment, the present invention concerns a method for producing virus, comprising the steps of:
(a) providing an immortalized avian cell line;
(b) infecting said immortalized avian cell line with a virus to be produced; and
(c) cultivating the said infected avian cell line under conditions which are enabling virus amplification;
wherein said immortalized avian cell line is selected in the group consisting of immortalized avian cell line deposited at the European Collection of Cell Cultures (ECACC) under accession number 08060502, an immortalized avian cell line deposited at the ECACC under accession number 08060501 and derivatives thereof.

According to another embodiment, the present invention relates to an immortalized avian cell line expressing avian telomerase reverse transcriptase (TERT) selected in the group consisting of an immortalized avian cell line deposited at the European Collection of Cell Cultures (ECACC) under accession number 08060502, an immortalized avian cell line deposited at the ECACC under accession number 08060501 and derivatives thereof. These cell lines have been generated from primary *Cairina moschata* cells as disclosed in WO2007/077256 by random insertion of the avian TERT nucleic acid molecule (SEQ ID NO: 1) into the *Cairina moschata* primary avian cells genome.

Surprisingly, these immortalized avian cell lines expressing avian telomerase reverse transcriptase (TERT) have distinct properties, and more particularly distinguish one from another by their virus strain amplification feature.

According to one special embodiment, the immortalized avian cell line of the invention is able of amplifying at least one Flaviviridae strain while being unable of amplifying Vaccinia virus strain Copenhagen (VV-COP) (GOEBEL et al. 1990; Genbank accession number M35027.1) nor Modified Vaccinia virus Ankara (MVA) (Collection Nationale de Cultures de Microorganismes (CNCM) under depositary N° I-721).

Detailed informations regarding assays used to determine whether an immortalized avian cell line is or not able of amplifying one specific virus strain are given further below.

According to preferred embodiment, the immortalized avian cell line of the invention able of amplifying at least one Flaviviridae strain while being unable of amplifying Vaccinia virus strain Copenhagen (W-COP) nor Modified Vaccinia virus Ankara (MVA) is an immortalized avian cell line expressing avian telomerase reverse transcriptase (TERT) deposited at the European Collection of Cell Cultures (ECACC) under accession number 08060502 or derivatives thereof.

According to preferred embodiment, the immortalized avian cell line deposited at the European Collection of Cell Cultures (ECACC) under accession number 08060502 or derivatives thereof is able of amplifying at least one Flaviviridae strain selected in the group consisting of Yellow fever virus strain (YFV) and Japanese encephalitis virus strain (JEV), and more particularly in the group consisting of YFV 17D strain (e.g. ref. 507 at HPA Culture Collections) and JEV Nakayama wild strain (e.g. ref. 502 at HPA Culture Collections).

According to preferred embodiment, the immortalized avian cell line deposited at the European Collection of Cell Cultures (ECACC) under accession number 08060502 or derivatives thereof is able of amplifying Yellow fever virus strain (YFV) and Japanese encephalitis virus strain (JEV).

According to another special embodiment, the immortalized avian cell line of the invention is able of amplifying (i) at least one Flaviviridae strain and (ii) at least one Poxviridae strain.

According to preferred embodiment, the immortalized avian cell line of the invention able of amplifying at least one Flaviviridae strain and at least one Poxviridae strain is an immortalized avian cell line expressing avian telomerase reverse transcriptase (TERT) deposited at the European Collection of Cell Cultures (ECACC) under accession number 08060501 or derivatives thereof.

According to preferred embodiment, the immortalized avian cell line deposited at the European Collection of Cell Cultures (ECACC) under accession number 08060501 or derivatives thereof is able of amplifying (i) at least one Flaviviridae strain selected in the group consisting of Yellow fever virus strain (YFV) and Japanese encephalitis virus strain (JEV), and more particularly in the group consisting of YFV 17D strain (e.g. ref. 507 at HPA Culture Collections) and JEV Nakayama wild strain (e.g. ref. 502 at HPA Culture Collections), and (ii) at least one Poxviridae strain selected in the group consisting of Vaccinia virus strain Copenhagen (VV-COP) (GOEBEL et al. 1990; Genbank accession number M35027.1) and Modified Vaccinia virus Ankara (MVA) (Collection Nationale de Cultures de Microorganismes (CNCM) under depositary N° I-721).

According to preferred embodiment, the immortalized avian cell line deposited at the European Collection of Cell Cultures (ECACC) under accession number 08060501 or derivatives thereof is able of amplifying Yellow fever virus strain (YFV), Japanese encephalitis virus strain (JEV), Vaccinia virus strain Copenhagen (VV-COP) and Modified Vaccinia virus Ankara (MVA)

Derivatives of the deposited *Cairina moschata* immortalized avian cell lines of the invention refer to *Cairina moschata* immortalized avian cell lines derived from the deposited ones by, for example:
- subcloning of the said deposited *Cairina moschata* immortalized avian cell line (ECACC 08060502 or ECACC 08060501);
- adaptation of the said deposited *Cairina moschata* immortalized avian cell line (ECACC 08060502 or ECACC 08060501) to a specific culture medium (e.g. medium allowing the growth of the cell line in suspension) and/or to specific culture conditions (e.g. temperature; % $CO_2$):
- deletion or mutation of one or more genes of *Cairina moschata* involved in saccharide fucose modification (HARUE IMAI-NISHIYA et al., *BMC Biotechnology* (2007)) in order to produced non-fucosylated proteins, and more particularly non-fucosylated antibodies (according to preferred embodiment, said derivatives of the deposited *Cairina moschata* immortalized avian cell line are obtained by deletion or mutation of α1,6-fucosyltransferase (FUT8) and/or GDP-mannose 4,6-dehydratase (GMD) genes;
- deletion or mutation of one or more genes of *Cairina moschata* involved in interferon resistance in order to reduce the immune response of the cell line (according to preferred embodiment, said derivatives of the deposited *Cairina moschata* immortalized avian cell line are obtained by deletion or mutation of gene(s) selected in the group consisting of STAT1 gene, STAT2 gene, STAT3 gene and STAT5 gene);
- overexpression of one or more *Cairina moschata*'s anti-apoptotic gene(s), or transformation with one or more exogenous anti-apoptotic gene(s) in order to render the cell line more resistant to the culture conditions, in particular for maintaining confluence (according to preferred embodiment, said anti-apoptotic gene(s) is selected in the group consisting of p19E1B human adenovirus gene, bcl-2 gene, mcl-1 gene, Bcl-xL gene, Bcl-w gene, a1 gene, ICP34.5 herpes simplex virus gene and p35 baculovirus gene);
- overexpression of one or more *Cairina moschata*'s genes involved in controlling the cell cycle using vectors which are suitable for increasing the rate of proliferation (according to preferred embodiment, said gene(s) involved in controlling the cell cycle, is selected in the group consisting of p53 gene, p21 gene, p27 gene and p57 gene);
- modifying the viral sensitivity spectrum of the cell line by transformation with one or more genes which encode receptors for the viruses of interest, with a view to multiplying these viruses (according to preferred embodiment, said gene(s) which encode receptors for the viruses of interest, is gene(s) which encode measles virus CD46 receptor).

According to preferred embodiment said ECACC 08060502 derivatives are able of amplifying at least one Flaviviridae strain while being unable of amplifying Vaccinia virus strain Copenhagen (VV-COP) nor Modified Vaccinia virus Ankara (MVA).

According to preferred embodiment said ECACC 08060501 derivatives are capable of amplifying (i) at least one Flaviviridae strain and (ii) at least one Poxviridae strain.

According to preferred embodiment, the immortalized avian cell lines of the invention are adherent cell lines.

According to another preferred embodiment, the immortalized avian cell lines of the invention are non-adherent cell lines which proliferate in suspension, in presence or not of (micro)carriers. The (micro)carriers used according to the invention can be made of dextran, collagen, polystyrene, polyacrylamide, gelatine, glass, cellulose, polyethylene and/or plastic. (Micro)carriers are commercially available such as e.g. Cytodex™ microcarriers (Pharmacia), Cytopore™ microcarriers (GE Healthcare Life Sciences), Hillex™ microcarriers (SoloHill Enginnering), Nunc 2D MicroHex™ microcarriers Nunclon™ (Thermo Fisher Scientific), ProNectin™ microcarriers (SoloHill Enginnering), FibraCell™ discs (New Brunswick Scientific), BioNocII™ microcarriers (Cesco Bioengineering) and CultiSpher-S™ microcarriers (Percell Biolytica).

The present invention also relates to the use of an immortalized avian cell line of the invention for the production of viruses and proteins.

As used throughout the entire application, "viruses" includes viruses selected in the group consisting of Flaviviridae, Poxviridae, flu viruses, Paramyxoviridae, adenovirus, adeno-associated virus (AAV), retrovirus (such as e.g. Rous sarcoma virus (RSV); human immunodeficiency virus (HIV)), hepadnaviruses (such as e.g. hepatitis B virus), herpes viruses (such as e.g. HSV-1; HSV-2), reoviruses (such as e.g. rotaviruses), coronaviruses (such as e.g. human SARS-CoV; HCoV-NL63), and alphaviruses (such as e.g. chikungunya; Ross river virus (RRV). The viruses can be wild type, attenuated, recombinant and/or temperature sensitive viruses.

The Flaviviridae and Poxviridae have been defined above.

According to the invention, the Flaviviridae is a wild type, attenuated, recombinant and/or temperature sensitive Flaviviridae.

According to the invention, the Poxviridae is a wild type, attenuated, recombinant and/or temperature sensitive Poxviridae.

As used throughout the entire application, "attenuated virus" refers to any virus that has been modified so that its pathogenicity in the intended subject is substantially reduced. Preferably, the virus is attenuated to the point it is nonpathogenic from a clinical standpoint, i.e. that subjects exposed to the virus do not exhibit a statistically significant increased level of pathology relative to control subjects. Several experimental approaches to attenuation of wild type Flaviviridae pathogens have been described (see e.g. PUGACHEV et al., *Int J. Parasitol.* 33:567-582 (2003)). For example, it has been found that mutations in certain amino acids of the envelope proteins of chimeric Flaviviridae including capsid and non-structural proteins of YFV and membrane and envelope proteins of JEV, a DENV, or West Nile virus decrease viscerotropism (see e.g. WO2003/103571 and WO2004/045529).

As used throughout the entire application, "recombinant virus" refers to a virus comprising an exogenous sequence inserted in its genome. As used herein, "exogenous sequence" refers to a nucleic acid molecule which is not naturally present in the parent virus. "Recombinant virus" can refer to a virus consisting of a virus in which one or more structural proteins has been replaced with foreign nucleic acid sequence of eukaryotic, prokaryotic, viral origin (e.g. structural protein(s) of a second virus). Therefore, according to the invention, "recombinant virus" can be also indifferently called "chimeric virus" or "hybrid virus". Notably, in the case of Flaviviridae, chimeric Flaviviridae can consist of a first Flaviviridae (e.g. a YFV such as for instance YFV 17D strain as previously described) in which the prM and E proteins have been replaced with the prM and E proteins of a second virus (e.g. a JEV, WNV, DENV, St. Louis encephalitis virus or TBEV as previously described). ChimeriVax™ technology has been used to create chimeric vaccine candidates against medically important Flaviviridae. It employs the YFV 17D vaccine virus as a vector in which the prM-E genes are replaced with the prM-E genes from a heterologous Flaviviridae such as JEV, DENV, WNV or St. Louis encephalitis viruses (MONATH et al., *Vaccine* 20:1004-1018 (2002); PUGACHEV et al., *Int. J. Parasitol.* 33:567-582 (2003); GUIRAKHOO et al., *J. Virol.* 78:4761-4775 (2004)). The ChimeriVax™-JEV vaccine comprising the prM-E genes from the SA14-14-2 virus (i.e. live attenuated JEV vaccine used in China), was successfully tested in preclinical and Phase I and II clinical trials. Similarly, successful Phase I clinical trials have been conducted with a ChimeriVax™-WNV vaccine candidate which comprises the prM-E sequence from a WNV (i.e. NY99 strain) with three specific amino acid changes incorporated into the E protein to increase attenuation (ARROYO et al., *J. Virol.* 78:12497-12507 (2004)). As other examples, chimeric Flaviviridae can also be chimeric Flaviviridae as described in WO2006/068307, WO2002/102828, EP0977587, WO98/37911, WO93/06214, U.S. Pat. No. 7,569,383 and WO01/39802.

Advantageously, the recombinant virus can further comprise the elements necessary for the expression of the exogenous sequence(s). The elements necessary for the expression comprise of the set of elements allowing the transcription of a nucleotide sequence to RNA and the translation of a mRNA to a polypeptide, in particular the promoter sequences and/or regulatory sequences which are effective in the cell to be infected by the recombinant virus, and optionally the sequences required to allow the excretion or the expression at the surface of the cells for said polypeptide. These elements may be inducible or constitutive. Of course, the promoter is adapted to the recombinant virus selected and to the host cell. The literature provides a large amount of information relating to such promoter sequences. The elements necessary can, in addition, include additional elements which improve the expression of the exogenous sequence or its maintenance in the host cell. There may be mentioned in particular the intron sequences, secretion signal sequences, nuclear localization sequences, internal sites for reinitiation of translation of the IRES type, poly A sequences for termination of transcription.

As used throughout the entire application, "temperature sensitive virus" refers to a virus derivative which has an impaired growth at or above a certain temperature at which the wild type has a normal growth. As examples, the temperature sensitive viruses as described in BOYD O. et al. (*Virology* April 10; 399(2):221-30 (2010)), EP 0 157 528 (smallpox temperature sensitive virus), and DRILLIEN R. et al. (*Virology* 119, 372-381 (1982)), can be cited.

According to the invention, "Flu viruses" (also called influenza viruses) includes influenza type A virus and its subtypes, influenza type B virus and influenza type C virus. "Subtypes of influenza type A virus" include the different combinations of HA and NA proteins possible. 19 classes of NA proteins (classified H1-H15) and 9 classes of NA proteins (classified N1-N9) have been identified in influenza type A viruses. As examples, subtypes of influenza type A virus can be H1N1 virus, H1N2 virus, H3N2 virus, H3N8 virus, H5N1 virus, H7N2 virus, H7N3 virus, H7N7 virus and H9N2 virus. Further information on the nucleotide sequences of the genomes of flu viruses can be obtained from publicly accessible gene databases such as www.flugenome.org/. Further information on the nucleotide sequences of the genomes of influenza type A viruses can also be obtained from publicly accessible gene databases such as GenBank, EMBL or LANL: e.g. J02144; J02146; J02148; J02151; V00603; V01099; V01104; V01106. Further information on the nucleotide sequences of the genomes of influenza type B viruses can also be obtained from publicly accessible gene databases such as GenBank, EMBL or LANL: e.g. J02094; J02095; J02096; K00423; K01395; M20168; M20170; M20172. Further information on the nucleotide sequences of the genomes of influenza type C viruses can also be obtained from publicly accessible gene databases such as GenBank, EMBL or LANL: e.g. K01689; M10087; M17700. Further information regarding attenuated flu virus vaccines can be found in HICKLING J. (A review of production for influenza virus vaccines, and their suitability for deployment in developing countries for influenza pandemic preparedness, Initiative for vaccine research, World Health Organisation (WHO) (2006); www.who.int/vaccine) and RUDENKO L. G. et al. (*Vaccine* 19(2-3), 308-318 (2000)). Further information regarding attenuated cold-adapted and temperature-sensitive flu virus vaccine such as for instance FluMist® (MedImmune Vaccines) can be found in GLEZEN W. (*Expert Rev. Vaccines* 3(2):131-9 (2004)).

According to the invention, "Paramyxoviridae" include Avulaviruses, Henipaviruses, Morbilliviruses, Respiroviruses, Rubulaviruses, Pneumoviruses and Metapneumoviruses. Avulaviruses include Newcastle disease virus (NDV) also called avian paramyxovirus virus 1 (APMV-1). Henipaviruses include Hendra virus (HeV) and Nipah virus (NiV). Morbilliviruses include measles virus (MV) of strains: Edmonston B strain (ENDERS J. F. and T. C. PEEBLES, Proc. Soc. Exp. Biol. Med. 86:277-286 (1954)), Edmonston A and B attenuated strains (GRIFFIN D. and Bellini W., in B. Fields, D. Knipe et al. (ed.), Virology, vol. 2, 1267-1312, Lippincott-Raven Publishers, Philadelphia (1996)), Schwarz/Moraten attenuated strain (GRIFFIN D. and Bellini W., Measles virus, in B. Fields, D. Knipe, et al. (ed.), Virology, vol. 2, 1267-1312, Lippincott-Raven Publishers, Philadelphia (1996); commercialized by Aventis Pasteur under Rouvax™) and attenuated MV strains as described in EP0540135, WO2008/086042 or WO99/49017. Respiroviruses include Sendai virus (SeV, also called murine parainfluenza virus 1), bovine parainfluenza virus 3 (BPIV-3), human parainfluenza virus 1 (HPIV-1) and human parainfluenza virus 3 (HPIV-3). Rubulaviruses include human parainfluenza virus 2 (HPIV-2), human parainfluenza virus 4a (HPIV-4a), human parainfluenza virus 4b (HPIV-4b) and mumps virus. Pneumoviruses include human respiratory syncytial virus A2 (HRSV-A2), human respiratory syncytial virus B1 (HRSV-B1) and human respiratory syncytial virus S2 (HRSV-S2). Metapneumoviruses include human metapneumovirus (HMPV).

As used throughout the entire application, "proteins" include:
- antibodies (e.g. rituximab; trastuzumab; cetuximab; milatuzumab; eculizumab; tocilizumab; nimotuzumab; golimumab; ramcirumab; bapineuzumab; infliximab; bevacizumab; adalimumab; ranibizumab; palivizumab; omalizumab; natalizumab; panitumumab; abciximab; efalizumab; certolizumab; tocilizumab; ustenkinumab),
- receptor ligands (e.g. hormones; cytokines; growth factors),
- hormones (e.g. adrenocorticotropic hormone (ACTH); antidiuretic hormone (ADH, vasopressin); atrial-natriuretic peptide (ANP); calcitonin; cholecystokinin (CCK); corticotropin-releasing hormone (CRH); glucagon; gonadotropin-releasing hormone (GnRH); growth hormone releasing hormone (GHRH); oxytocin; secretin; somatostatin; thyrotropin-releasing hormone (TRH); erythropoietin (EPO); follicle-stimulating hormone (FSH); growth hormone (GH); human chorionic gonadotropin (HCG); insulin; Insulin-like growth factor-1 (IGF-1); luteinizing hormone (LH); parathyroid hormone (PTH); prolactin (PRL); thrombopoitin; thyroid-stimulating hormone (TSH); Testosterone; dihydrotestosterone (DHT); andostenedione; dehydroepiandrosterone (DHEA); testosterone; calciferol; calcitriol; estradiol; cortisol; aldosterone; progesterone; adrenaline (epinephrine); dopamine; melatonin; noradrenaline (norepinephrine, NE); triiodothyronine (T3); thyroxine (T4); serotonin),
- cytokines (e.g. interleukins (IL-1; IL-2; IL-3; IL-4; IL-5; IL-6; IL-7; IL-8; IL-9; IL10; IL-11; IL-12; IL13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33); chemokines (CC chemokine ligand 1 (CCL-1); CCL-2; CCL-3 (also called macrophage inflammatory protein 1 alpha (MIP-1α)); CCL-4 (also called macrophage inflammatory protein 1 beta (MIP-1β)); CCL-5 (also called RANTES); CCL-6; CCL7; CCL-8; CCL-9; CCL-10; CCL-11; CCL-12; CCL-13; CCL-14; CCL-15; CCL-16; CCL-17; CCL-18; CCL-19; CCL-20; CCL21; CCL-22; CCL-23; CCL-24; CCL-25; CCL-26; CCL-27; CCL-28; CXC chemokin 1 (CXCL-1); CXCL-2; CXCL-3; CXCL-4 (also called platelet factor 4 (PF4)); CXCL-5; CXCL-6; CXCL-7; CXCL-8; CXCL-9; CXCL-10; CXCL-11; CXCL-12; CXCL-13; CXCL-14; CXCL-15; CXCL-16; CXCL-17; C chemokin 1 (XCL-1); XCL-2; $CX_3C$ chemokin 1 ($CX_3CL$-1); interferons (IFN-alpha; IFN-beta; IFN-gamma); tumor necrosis factors (TNF-alpha; TNF-beta)),
- growth factors (e.g. epidermal growth factor (EGF); vascular endothelial growth factor (VEGF); Bone morphogenetic proteins (BMPs); Erythropoietin (EPO); Fibroblast growth factor (FGF); granulocyte colony-stimulating factor (G-CSF); granulocyte-macrophage colony-stimulating factor (GM-CSF); human pluripotent granulocyte colony-stimulating factor (hPG-CSF); macrophage colony-stimulating factor (M-CSF); growth differentiation factor-9 (GDF9); macrophage migration inhibitory factor (MIF); insulin-like growth factor (IGF); myostatin (GDF-8); nerve growth factor (NGF); platelet-derived growth factor (PDGF); thrombopoietin (TPO); transforming growth factor alpha (TGF-α); transforming growth factor beta (TGF-β); placental growth factor (PlGF)), antigens (e.g. antigens of the MHC; leukocyte function associated antigen-1 (LFA-1)),
- cell adhesion molecules (e.g. intercellular cell adhesion molecule (ICAM-1); neural cell adhesion molecules (NCAMs); vascular cell adhesion molecule (VCAM-1); platelet-endothelial cell adhesion molecule (PECAM-1); nectins; synaptic cell adhesion molecules (SynCAMs)),
- blood clotting factors (e.g. Factor VIII; Factor IX; tPA),
- enzymes (e.g. alpha-amylase; beta-amylase; cellulose; beta-Glucanase; beta-glucosidase; dextranase; dextrinase; dlucoamylase; hemmicellulase; pentosanase; xylanase; invertase; lactase; naringinase; pectinase; pullulanase; acid proteinase; alkaline protease; bromelain; pepsin; aminopeptidase; endopeptidase; subtilisin; aminoacylase; glutaminase; lysozyme; penicillin acylase; isomerase; alcohol dehydrogenase; catalase; chloroperoxidase; peroxidase; acetolactate decarboxylase; histidase; cyclodextrin glycosyltransferase), fragments thereof and combinations thereof.

According to one special embodiment, the invention relates to the use of the immortalized avian cell line deposited at the European Collection of Cell Cultures (ECACC) under accession number 08060502 and derivatives thereof, for the production of viruses and proteins.

According to preferred embodiment, the invention relates to the use of the immortalized avian cell line deposited at the European Collection of Cell Cultures (ECACC) under accession number 08060502 and derivatives thereof, for the production of viruses and the said virus is a Flaviviridae, preferably selected in the group consisting of Yellow fever virus strain (YFV) and Japanese encephalitis virus strain (JEV), and more particularly in the group consisting of YFV 17D strain and JEV Nakayama wild strain. Example 3 describes a preferred method for producing YFV 17D strain and JEV Nakayama wild strain.

According to another preferred embodiment, the invention relates to the use of the immortalized avian cell line deposited at the European Collection of Cell Cultures (ECACC) under accession number 08060502 and derivatives thereof, for the production of proteins, such as for example those selected from the group consisting of cytokines, antibodies and hormones, and even more particularly in the group consisting of IL-2, rituximab and erythropoietin (EPO). A preferred method for producing IL-2 is described in Example 5. A preferred method for producing rituximab is described in Example 6. A preferred method for producing EPO is described in Example 7.

According to another special embodiment, the invention relates to the use of the immortalized avian cell line deposited at the European Collection of Cell Cultures (ECACC) under accession number 08060501 and derivatives thereof, for the production of viruses and proteins.

According to preferred embodiment, the invention relates to the use of the immortalized avian cell line deposited at the European Collection of Cell Cultures (ECACC) under accession number 08060501 and derivatives thereof, for the production of viruses and the said virus is a Flaviviridae, preferably selected in the group consisting of Yellow fever virus strain (YFV) and Japanese encephalitis virus strain (JEV), and more particularly in the group consisting of YFV 17D strain and JEV Nakayama wild strain. Example 3 describes a preferred method for producing YFV 17D strain and JEV Nakayama wild strain.

According to another preferred embodiment, the invention relates to the use of the immortalized avian cell line deposited at the European Collection of Cell Cultures (ECACC) under accession number 08060501 and derivatives thereof, for the production of viruses and the said virus is a Poxviridae, preferably selected in the group consisting of Vaccinia virus strain Copenhagen (VV-COP) and Modified Vaccinia virus Ankara (MVA). Example 4 describes a preferred method for producing VV-COP and MVA.

According to another preferred embodiment, the invention relates to the use of the immortalized avian cell line deposited at the European Collection of Cell Cultures (ECACC) under accession number 08060501 and derivatives thereof, for the production of proteins, such as for example those selected from the group consisting of cytokines, antibodies and hormones, and even more particularly in the group consisting of IL-2, rituximab and erythropoietin (EPO). A preferred method for producing IL-2 is described in Example 5. A preferred method for producing rituximab is described in Example 6. A preferred method for producing EPO is described in Example 7.

The present invention also relates to a method for producing a virus comprising the steps of:
a) infecting an immortalized avian cell line deposited at the European Collection of Cell Cultures (ECACC) under accession number 08060502, with a virus; and
b) cultivating the infected avian cell line under conditions which are enabling virus amplification.

The present invention further relates to a method for producing and purifying a wild type, an attenuated and/or a recombinant Orthopoxvirus, comprising the following steps:
a) preparing a culture of packaging cells;
b) infecting the packaging cell culture with an Orthopoxvirus;
c) culturing the infected packaging cells until progeny Orthopoxvirus is produced;
d) incubation in presence of one or more nucleases;
e) recovering the Orthopoxviruses from the culture supernatant and/or the packaging cells;
f) adding monovalent salts to the Orthopoxviruses recovered in step e) under suitable conditions to inhibit the nuclease(s) activity and to avoid the adsorption of said Orthopoxviruses to the anion exchange adsorbent in step g);
g) contacting the mixture obtained in step f) with an anion exchange adsorbent under suitable conditions to allow the capture of nucleic acids;
h) clarifying the mixture obtained in step g) under suitable conditions to allow the withdrawal of the cellular debris;
i) washing of the anion exchange adsorbent with a solution comprising monovalent salts under suitable conditions to recover the remained Orthopoxviruses in the flow through;
j) concentrating the flow through obtained in step h) and the flow through obtained in step i);
k) diafiltrating the fraction comprising the Orthopoxviruses obtained in step j), wherein said packaging cells are *Cairina moschata* immortalized avian cell lines comprising a nucleic acid sequence coding a telomerase reverse transcriptase (TERT) covered by patent application WO 2007/077256. Are particularly preferred, the following immortalized avian cell lines:
T3-17490 as deposited at the European Collection of Cell Cultures (ECACC) under accession number 08060502 (see FIGS. 2, 3 and 4) or a derivative thereof;
T6-17490 as deposited at the European Collection of Cell Cultures (ECACC) under accession number 08060501 (see FIGS. 5, 6 and 7) or a derivative thereof.

According to preferred embodiment, the virus is a Flaviviridae, preferably selected in the group consisting of Yellow fever virus strain (YFV) and Japanese encephalitis virus strain (JEV), and more particularly in the group consisting of YFV 17D strain and JEV Nakayama wild strain. Example 3 describes a preferred method for producing YFV 17D strain and JEV Nakayama wild strain.

According to another special embodiment, the invention relates to a method for producing a virus comprising the steps of:
a) infecting an immortalized avian cell line deposited at the European Collection of Cell Cultures (ECACC) under accession number 08060501, with a virus; and
b) cultivating the infected avian cell line under conditions which are enabling virus amplification.

According to preferred embodiment, the produced virus is a Flaviviridae, preferably selected in the group consisting of Yellow fever virus strain (YFV) and Japanese encephalitis virus strain (JEV), and more particularly in the group consisting of YFV 17D strain and JEV Nakayama wild strain. Example 3 describes a preferred method for producing YFV 17D strain and JEV Nakayama wild strain.

According to another preferred embodiment, the produced virus is a Poxviridae, preferably selected in the group consisting of Vaccinia virus strain Copenhagen (VV-COP) and Modified Vaccinia virus Ankara (MVA). Example 4 describes a preferred method for producing VV-COP and MVA.

The avian cell lines of the invention are preferably infected at a temperature comprised between 30° C. and 37° C., and more preferably at 37° C. as described in Example 3 and 4. Step a) of infection of the cell lines of the invention with a virus is performed in an appropriate cell culture medium. The cell culture medium can be for instance Dulbecco's Modified Eagle's Medium (DMEM, Invitrogen) or Basal Medium Eagle (BME, Invitrogen) which can be optionally supplemented with e.g. serum (e.g. Fetal Calf Serum (FCS)) and/or amino acid(s) (e.g. L-Glutamine). The cell culture medium can also be a medium free from animal product. Many media free from animal product have been already described and some of them are commercially available such as for instance 293 SFM II; 293-F Cells, SFM Adapted; 293-H Cells, SFM Adapted; 293Fectin™ Transfection Reagent; CD 293 AGT™; CD 293 Medium; FreeStyle™ 293 Expression System; FreeStyle™ 293 Medium; FreeStyle™ 293-F Cells, SFM Adapted; VP-SFM; VP-SFM AGT™; Adenovirus Expression Medium (AEM) Growth Medium for PER.C6® Cells; CD 293 AGT™; CD 293 Medium; COS-7L Cells, SFM Adapted; EPISERF® Medium; OptiPro™ SFM (all available from Invitrogen). As described in Example 3 and in Example 4, preferred cell culture medium used for the infection of the avian cell lines of the invention is BME (Invitrogen) supplemented with FCS and L-Glutamine.

The cell lines of the present invention are infected with a virus at a Multiplicity of Infection (MOI) which depends on the produced virus. For instance, a Flaviviridae is seeded into the avian cell lines of the invention at a MOI which is preferably comprised between about 0.001 and 0.1. More particularly, when the produced Flaviviridae is YFV or JEV, the MOI is more preferably about 0.001 as described in Example 3, FIG. 7A, FIG. 8A, FIG. 9A and FIG. 10A. As another example, a Poxviridae is seeded into the avian cell lines of the invention at a MOI which is preferably comprised between about 0.0001 and 0.1. More particularly, when the produced Poxviridae is VV-COP, the MOI is more preferably about 0.0001 as described in Example 4 and FIG. 11B. When the produced Poxviridae is a MVA, the MOI is more preferably about 0.05 as described in Example 4 and FIG. 11A.

The infected cell lines are then cultivated under conditions which are enabling virus amplification (i.e. step b)) meaning that the viral genome is transcribed, translated into viral proteins and packaged into infectious viral particles.

The infected cell lines can be cultivated as adherent cells to surfaces or in suspension, in presence or absence of (micro) carriers (as previously defined). Cell line culture can be done for instance in dishes, roller bottles or in bioreactors, using batch, fed-batch, continuous systems, hollow fiber, and the like. The infected avian cell lines of the invention are preferably cultivated at a temperature comprised between 30° C. and 37° C., and more preferably at 37° C. as described in Example 3 and 4. Step b) of culture of the infected avian cell lines is performed in an appropriate cell culture medium which can be the same or different from the cell culture medium used for the infection of the avian cell lines (in step a)). The infected avian cell lines are preferably cultivated for between 1 and 6 days depending on the virus. For instance, when the produced virus is YFV, the infected avian cell lines are more preferably cultivated for between 1 and 3 days as shown in FIG. 7A and FIG. 9A. As another example, when the produced virus is JEV, the infected avian cell lines are more preferably cultivated for between 1 and 4 days as shown in FIG. 8A and FIG. 10A. As another example, when the produced virus is VV-COP or a MVA, the infected avian cell lines are more preferably cultivated between 1 and 4 days as shown in FIG. 11 (A-B).

According to the invention, step a) of infection can be preceded by a step of culturing a cell line of the invention in an appropriate cell culture medium which can be the same or different from the cell culture medium used for the infection of the avian cell lines (in step a)) and from the cell culture medium used for the culture of the infected avian cell lines (in step b)). The avian cell lines are preferably cultivated for between 1 and 3 days, more preferably for 1 day before infection, at a temperature comprised between 30 and 37° C., more preferably at 37° C. as described in Example 3 and 4.

According to the invention, step b) of culture the infected cell line can be followed by a step of incubation in presence of one or more nucleases (i.e. endonuclease or exonucleases) in order to degrade the nucleic acids (e.g. DNA; RNA) present in solution. Nucleases preferably used according to the present invention are endonucleases. Endonucleases that can be used according to the invention can be classified based on their substrates as follows: deoxyribonucleases (DNases) which degrade DNA; ribonucleases (RNases) which degrade RNA; and endonucleases that degrade DNA and RNA. Endonucleases DNases include but are not limited to DNase I, DNase II and endodeoxyribonuclease IV. Endonucleases RNases include but are not limited to RNase I, RNase III, RNAse E, RNAse F and RNAse P. Endonucleases that degrade DNA and RNA include but are not limited to Benzonase®. Endonuclease preferably used according to the present invention is Benzonase®. Benzonase® degrades nucleic acid (e.g. DNA; RNA) by hydrolyzing internal phosphodiester bonds between specific nucleotides. Upon complete digestion, all free nucleic acids (e.g. DNA; RNA) present in solution are reduced to 5'-monophosphate terminated oligonucleotides which are 3 to 8 bases in length. Benzonaze® has no proteolytic activity. Benzonaze® used according to the present invention is preferably pharmaceutically acceptable. Pharmaceutically acceptable Benzonaze® are commercially available (e.g. Eurogentec under the reference ME-0280-10; Merck under the reference e.g. 1.01653.0001). According to the invention, the concentration of nuclease(s) used is in a range of 5 to 100 U/ml, preferably in a range of 5 to 50 U/ml, and more preferably 10 U/ml.

The viruses produced are then recovered from the supernatant and/or from the cells. When the produced viruses are recovered from the cells (i.e. from the cells only, or from the cells and from the supernatant), the step of recovering of the viruses produced can be preceded by a step allowing the disruption of the cell membrane. This step leads to the liberation of the viruses from the cells. The disruption of the cell membrane can be induced by various techniques well known by the one skilled in the art. These techniques comprise but are not limited to freeze/thaw, hypotonic lysis, sonication (by using a sonicator) and microfluidization (by using a microfluidizer). Sonicators are commercially available from e.g. Heraeus PSP, Biologics, Misonix or GlenMills. Preferred sonicators used according to the present invention are SONITUBE 20 kHz type SM 20-120-3 and SONITUBE 35 kHz type SM 35-400-3 (Heraeus PSP). Microfluidizers are commercially available from e.g. Microfluidics Corporation. The avian cell membrane can also be disrupted by using a using a SLM Aminco French press. The cell membrane can also be disrupted by using a high speed homogenizer. High speed homogenizers are commercially available from e.g. Silverson Machines or Ike-Labotechnik.

According to special embodiment of the invention, the viruses recovered are then purified. Purification of the viruses produced can comprise for instance one or more of the following steps:

A clarification allowing under suitable conditions the withdrawal of the cellular debris. Said clarification can be performed by e.g. depth filtration. Depth filtration includes but is not limited to the use of one or more commercially available products such as Sartopure® filters from Sartorius (e.g. Sartopure® PP2), CUNO Incorporated AP series depth filters (e.g. AP01), CUNO Incorporated CP series depth filters (e.g. CP10, CP30, CP50, CP60, CP70, CP90), CUNO Incorporated HP series depth filters (e.g. HP10, HP30, HP50, HP60, HP70, HP90), CUNO Incorporated Calif. series depth filters (e.g. CA10, CA30, CA50, CA60, CA70, CA90), CUNO Incorporated SP series depth filters (e.g. SP10, SP30, SP50, SP60, SP70, SP90), CUNO Delipid and Delipid Plus filters, Millipore Corporation CE series depth filters (e.g. CE15, CE20, CE25, CE30, CE35, CE40, CE45, CE50, CE70, CE75), Millipore Corporation DE series depth filters (e.g. DE25, DE30, DE35, DE40, DE45, DE50, DE55, DE560, DE65, DE70, DE75), Millipore Corporation HC filters (e.g. A1HC, B1HC, COHC), CUNO PolyNet™ Filters (e.g. PolyNet™ PB P050, P100, P200, P300, P400, P500, P700), Millipore Clarigard and Polygard filters, CUNO Life Assure filters, ManCel Associates depth filters (e.g. PR 12 UP, PR12, PR 5 UP); and PALL or SeitzSchenk Incorporated filters. In order to improve the clarification capacity of the available depth filtration units, it can be useful to couple two or more units with decreasing pore sizes. In this embodiment, the mixture to be clarified passes through the first depth filtration unit where the biggest contaminants are retained and subsequently passes through the second depth filtration unit. With this regard, the clarification is preferably performed by depth filtration, and more preferably over filters having a pore size 8 μm coupled to filters having a pore size of 5 μm. Preferred filters having a pore size of 8 μm and 5 μm used according to the present invention are Sartopure® filters commercially available from Sartorius (Sartopure® PP2). The depth filtration is preferably performed at a flow rate of 1 L/minute.

A concentration which can be performed by e.g. microfiltration or ultrafiltration. Microfiltration is a pressure driven membrane process that concentrates and purifies large molecules. More specifically, a solution is passed through filters whose pore size has been chosen to reject the virus in the retentate and allow small molecules (e.g. proteins) to pass through the filters into the permeate. Microfiltration reduces the volume of the extraction solution. Filters used according to the invention are preferably autoclavable commercially available filters such as for instance Prostak Microfiltration Modules (Millipore).

A diafiltration which is an improvement of microfiltration (as previously described) and involves diluting said fraction comprising the virus with a solution to effect a reduction in the concentration of the impurities in said fraction. The dilution of the fraction comprising the viruses allows washing out more of the impurities from said fraction. It is understood that the diafiltration may be carried out in a batch mode, semi-continuous mode, or a continuous mode. The diafiltration can be advantageously used to change the buffer in which the virus is comprised. For example, it can be useful to exchange the buffer used in the purification process against a pharmaceutically acceptable buffer. Filters used for the diafiltration according to the invention allow the rejection of the virus in the retentate and the passage of the small molecules (e.g. proteins) through the filters into the permeate. Such filters are preferably autoclavable commercially available filters such as for instance Prostak Microfiltration Modules (Millipore).

A chromatography using a cation or an anion exchange adsorbent, and preferably an anion exchange adsorbent. The functional groups of the anion exchange adsorbent can be primary, secondary, tertiary or quaternary amino group such as for instance dimethylaminoethyl (DMAE), diethylaminoethyl (DEAE), trimethylaminoethyl (TMAE), triethylaminoethyl (TEAE), the group —R—CH(OH)—CH$_2$—N+-(CH$_3$)$_3$ (also named Q group; see Streamline® resins, Pharmacia) or other groups such as for instance polyethyleneimine (PEI) that already have or will have a formal positive charge within the pH range of 7.0 to 9.0. The anion exchange adsorbent can consist in, but is not limited to, e.g. a beads-formed matrix or a membrane. When the anion exchange adsorbent consists in a beads-formed matrix, the matrix can be e.g. agarose, hydrophilic polymer, cellulose, dextran or silica. Chains (e.g. dextran chains) are coupled to the matrix. Functional groups as previously described are attached to the chains through chemically stable bonds (e.g. ether bonds). Anion exchange adsorbents consisting of beads-formed matrix used according to the invention are preferably autoclavable such as for instance UNOsphere® Q (BioRad), UNOsphere® S (BioRad), STREAMLINE™ Q Sepharose® XL (Amersham Biosciences), STREAMLINE™ SP Sepharose® XL (Amersham Biosciences) or BioSepra® Q hyperZ (Pall Corporation). When the anion exchange adsorbent consists in a membrane, the membrane used has a pore size lower than the size of the virus.

The wild type, attenuated, recombinant and/or temperature sensitive virus produced can be further inactivated so that the outer virion coat has been left intact but the replicative function has been destroyed. Preparation of said "whole-killed virus" can take the route of heat or chemicals. The chemicals used include for formaldehyde or beta-propiolactone and formalin (CHERTOVA E. et al., *AIDS Vaccine* (2001)).

According to one special embodiment, the invention relates to a method for producing proteins comprising the steps of:
a) contacting an immortalized avian cell line deposited at the European Collection of Cell Cultures (ECACC) under accession number 08060502, with at least one recombinant vector comprising a nucleotide sequence coding at least one protein; and
b) cultivating the avian cell line under conditions which are enabling the protein to be produced.

According to another special embodiment, the invention relates to a method for producing a protein comprising the steps of:
a) contacting an immortalized avian cell line deposited at the European Collection of Cell Cultures (ECACC) under accession number 08060501, with a recombinant vector comprising a nucleotide sequence coding the protein; and
b) cultivating the avian cell line under conditions which are enabling the protein to be produced.

According to the present invention, the recombinant vector can be of plasmid or viral origin and can, where appropriate, be combined with one or more substances which improve the transfectional efficiency and/or stability of the vector. These substances are widely documented in the literature which is available to the skilled person (see for example FEIGNER et al., *Proc. West. Pharmacol. Soc.* 32,115-121 (1987); HODGSON and SOLAIMAN, *Nature Biotechnology* 14, 339-342 (1996); REMY et al., *Bioconjugate Chemistry*, 5, 647-654 (1994)). According to the present invention, the recombinant vectors are expression vectors. In a general manner, they are known to the skilled person and, while a number of them are available commercially, it is also possible to construct them or to modify them using the techniques of genetic manipulation.

According to a preferred embodiment of the invention, the recombinant vector is a plasmid. Preferably, the plasmid which is used in the context of the present invention contains an origin of replication. The plasmid can additionally comprise a selection gene which enables the transfected cells to be selected or identified (complementation of an auxotrophic mutation, gene encoding resistance to an antibiotic, etc.). The plasmid can contain additional elements which improve its maintenance and/or its stability in the immortalized avian cell line of the invention. Examples of plasmids are described in Example 5, 6 and 7.

According to preferred embodiment of the invention, the produced protein is a cytokine, more particularly an interleukin, and even more particularly IL-2. A preferred method for producing IL-2 is described in Example 5.

According to another preferred embodiment of the invention, the produced protein is an antibody, and more particularly rituximab. Rituximab (Rituxan® or MabThera®) is a chimeric murine/human anti-CD20 monoclonal antibody. A preferred method for producing rituximab is described in Example 6.

According to another preferred embodiment of the invention, the produced protein is a hormone, and more particularly erythropoietin (EPO). A preferred method for producing EPO is described in Example 7.

According to a preferred embodiment of the invention, the methods for producing proteins and viruses are free from animal products (except the avian cell lines of the invention) and suitable for an aseptic industrial-scale manufacturing process to ensure a full compliance with regulatory requirements regarding sterility of vaccines. As used throughout the entire application, <<animal product>> refer to any compound or collection of compounds that was produced in or by an animal cell in a living organism.

The present invention also relates to a purified wild type, attenuated, recombinant and/or temperature sensitive virus obtained by the method as previously described.

The present invention also relates to a purified whole-killed virus obtained by the method as previously described.

The present invention also relates to a purified protein obtained by the method as previously described.

The present invention also relates to a pharmaceutical composition, and more particularly a vaccine, comprising a purified wild type, attenuated, recombinant, temperature sensitive and/or whole-killed virus obtained by the method as previously described.

The present invention also relates to a pharmaceutical composition comprising a purified protein obtained by the method as previously described.

As used herein, a "pharmaceutical composition" refers to a composition comprising a pharmaceutically acceptable carrier. Said pharmaceutically acceptable carrier is preferably isotonic, hypotonic or weakly hypertonic and has a relatively low ionic strength, such as for example a sucrose solution. Moreover, such a carrier may contain any solvent, or aqueous or partially aqueous liquid such as nonpyrogenic sterile water. The pH of the pharmaceutical composition is, in addition, adjusted and buffered so as to meet the requirements of use in vivo. The pharmaceutical compositions may also include a pharmaceutically acceptable diluent, adjuvant or excipient, as well as solubilizing, stabilizing and preserving agents. For injectable administration, a formulation in aqueous, non-aqueous or isotonic solution is preferred. It may be provided in a single dose or in a multidose in liquid or dry (powder, lyophilisate and the like) form which can be reconstituted at the time of use with an appropriate diluent.

To illustrate the invention, the following examples are provided. The examples are not intended to limit the scope of the invention in any way.

EXAMPLES

Example 1

Immortalized *Cairina moschata* Cell Line ECACC 08060502

Figure 1:
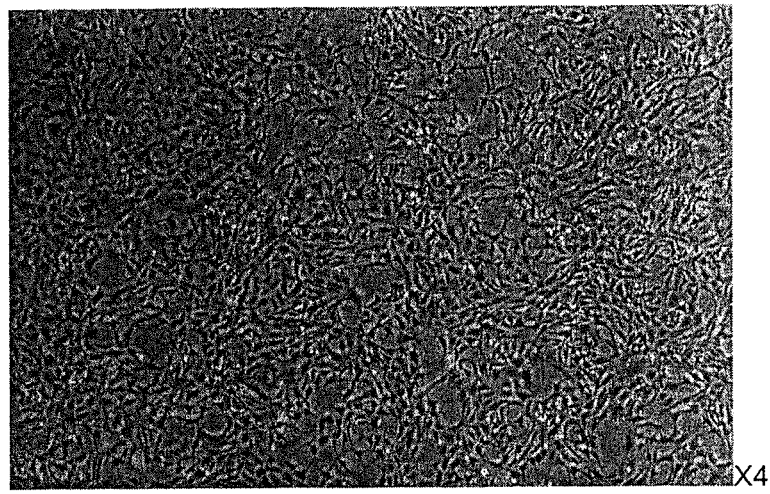
FIG. 1 depicts light microscopy imaging of the *Cairina moschata* immortalized avian cell line ECACC 08060502 (passage 39).
Figure 1:
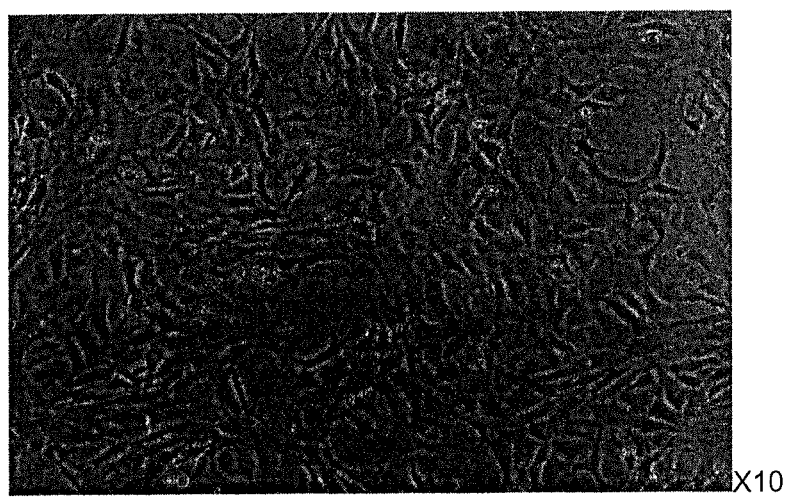
Figure 1:
Figure 2:
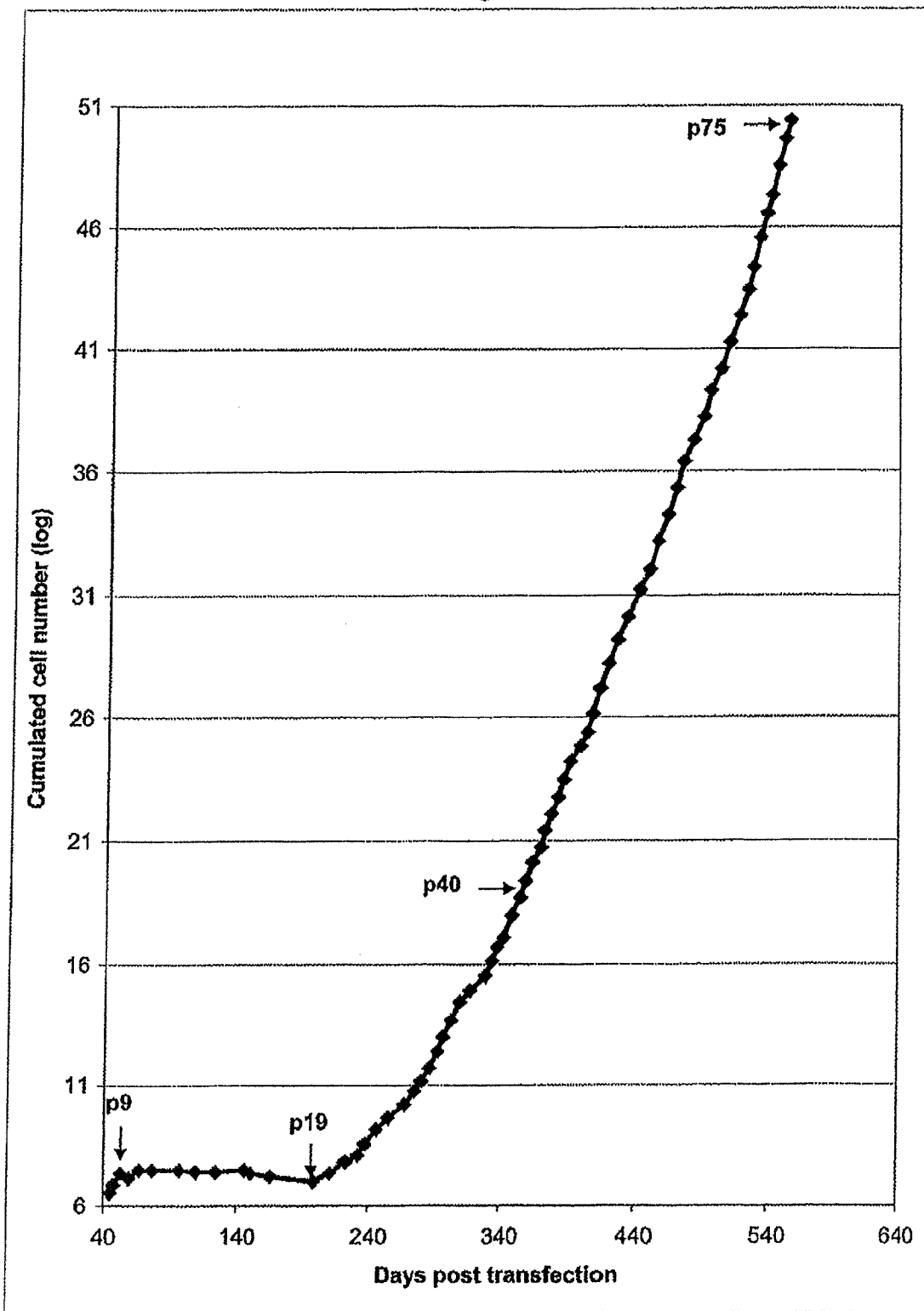
FIG. 2 depicts the *Cairina moschata* immortalized avian cell line ECACC 08060502 growth curve (from passage 7 to passage 75).
Figure 3:
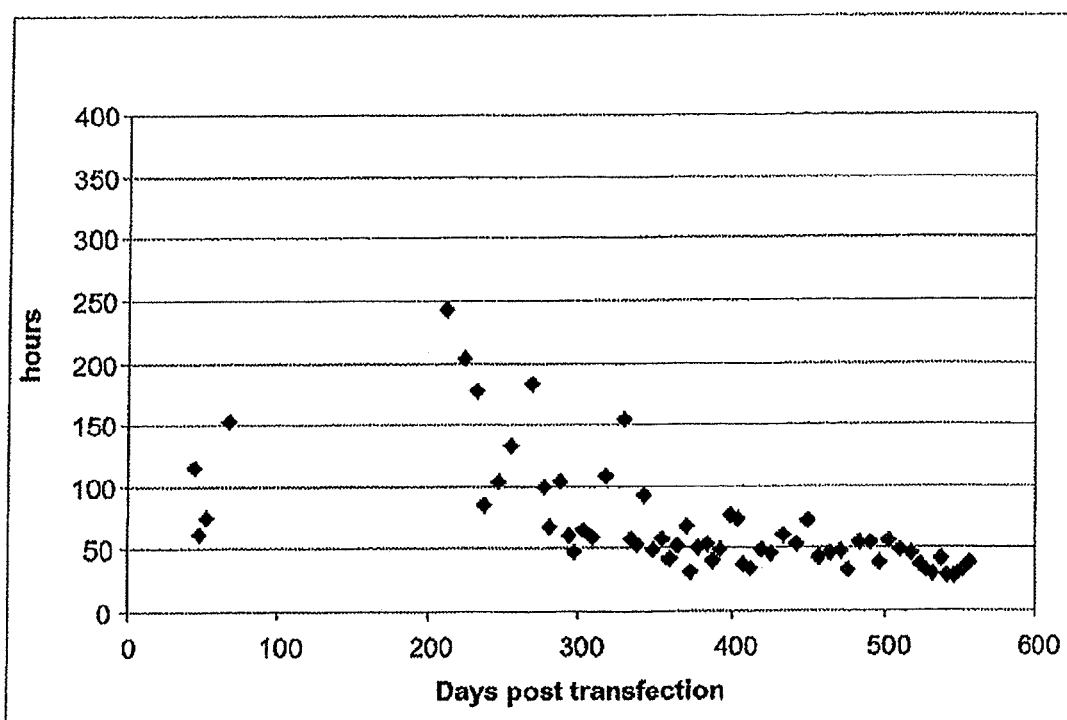
FIG. 3 depicts the *Cairina moschata* immortalized avian cell line ECACC 08060502 population doubling time evolution (from passage 7 to passage 75).

The *Cairina moschata* cells ECACC 08060502 (passage 39) have a homogenous fibroblast like morphology (FIG. 1). The static monolayer is stable up to 100% confluence and subject to contact inhibition. The cells were tested negative for mycoplasma contamination and for microbial contamination as well. The cell line growth curve (from passage 7 to passage 75) (FIG. 2) shows a continuous exponential growth phase from passage 19 to passage 75. Focusing on the evolution of the population doubling time (PDT), a progressive stabilisation and decrease is observed, in particular it can be noted that the PDT is stabilised under the 48 h mark during the 10 latest passages (FIG. 3). The corresponding number of population doublings (population doubling level, PDL) has been calculated by cumulating the 2 exponential growth phases: during the 75 passages the cells have undergone at least 147 population doublings (PD). The number of population doublings a primary cell can undergo before entering senescence is tissue and specie dependent. It is commonly admitted that the upper limit is situated between 50 and 60 PD. The *Cairina moschata* cell line ECACC 08060502 is therefore far beyond the Hayflick limit and is consequently referred as immortalized cell line.

N.B.:
The population doubling level (PDL) refers to the number of cell generations (biomass 2 fold increase). PDL calculation: PDL=Ln(final/initial cell number)/Ln(2);
The population doubling time (PDT), also called generation time, is the time needed for one population doubling. PDT calculation: PDT=Δt*Ln(2)/Ln(final/initial cell number).

Example 2

Immortalized *Cairina moschata* Cell Line ECACC 08060501

Figure 4:
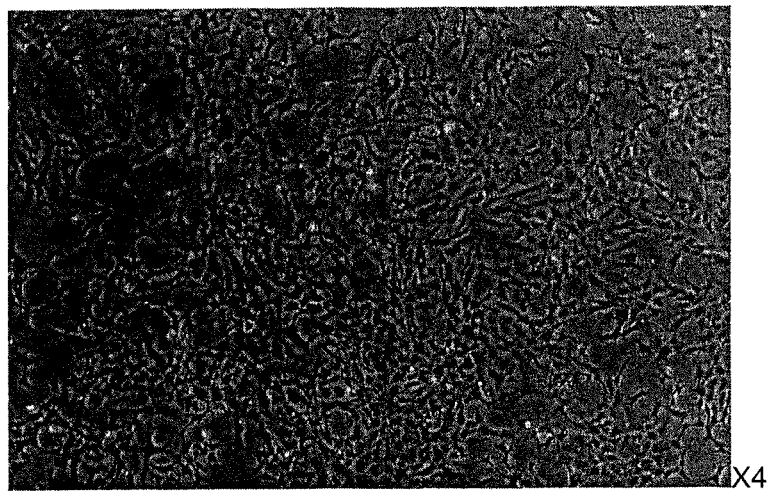
FIG. 4 depicts light microscopy imaging of the *Cairina moschata* immortalized avian cell line ECACC 08060501 (passage 45).
Figure 4:
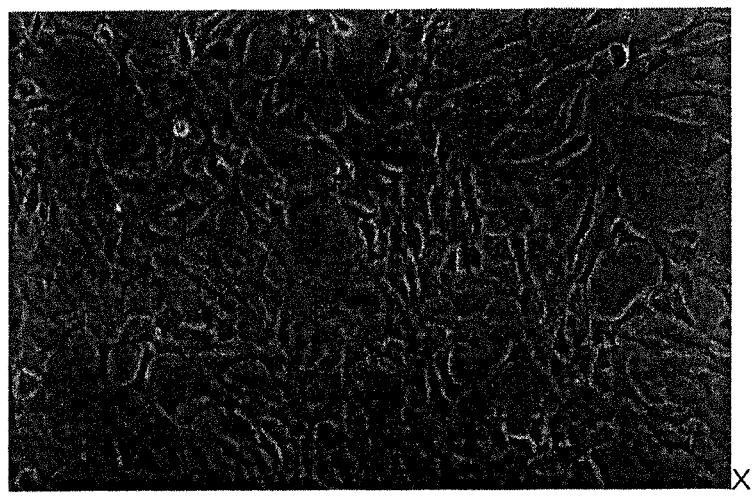
Figure 4:
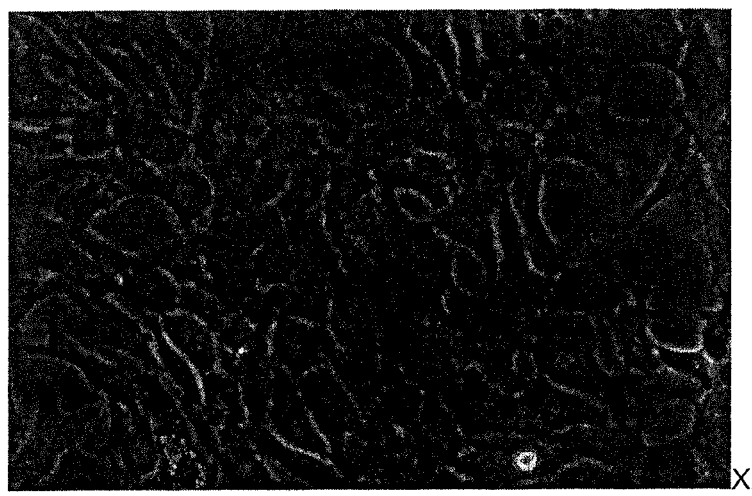
Figure 5:
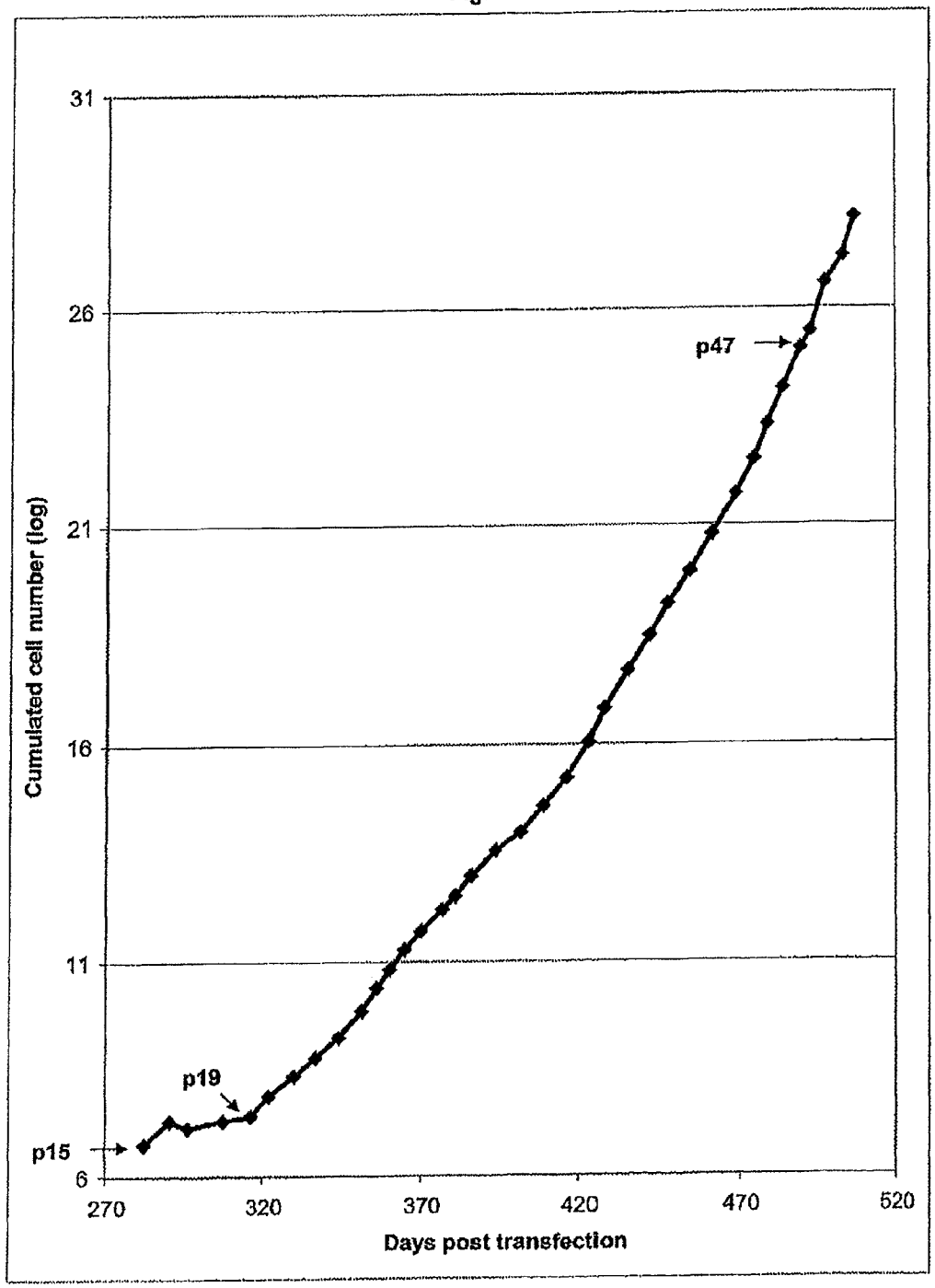
FIG. 5 depicts the *Cairina moschata* immortalized avian cell line ECACC 08060501 growth curve (from passage 15 to passage 51).
Figure 6:
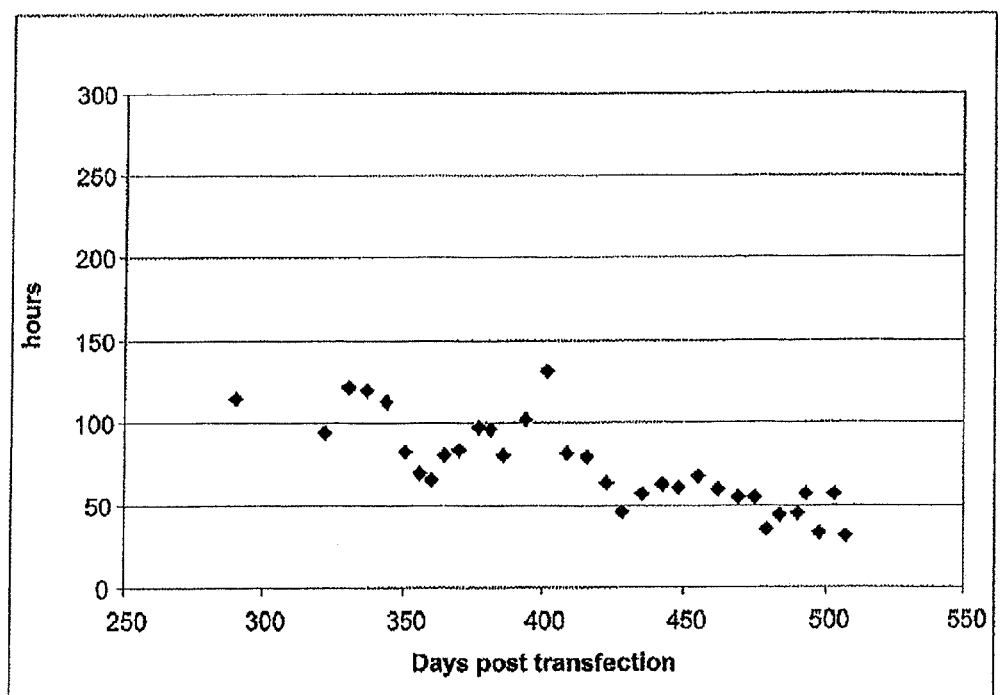
FIG. 6 depicts the *Cairina moschata* immortalized avian cell line ECACC 08060501 population doubling time evolution (from passage 16 to passage 51).

The *Cairina moschata* cells ECACC 08060501 (passage 45) have a homogenous fibroblast like morphology (FIG. 4). The static monolayer is stable up to 100% confluence and subject to contact inhibition. The cells were tested negative for mycoplasma contamination and for microbial contamination as well. The cell line growth curve (from passage 15 to passage 51) (FIG. 5) shows a continuous exponential growth phase from passage 19. During this period the measured population doubling time (PDT) was progressively decreasing. Average PDT passed from 94 h (passage 20 to 35) to 52 h (passage 36 to 51) (FIG. 6). The number of calculated population doublings (PDL) corresponding to the 51 passages is at least 71 population doublings. The *Cairina moschata* cell line ECACC 08060501 is therefore far beyond the Hayflick limit and is consequently referred as immortalized cell line.

N.B.
The population doubling level (PDL) refers to the number of cell generations (biomass 2 fold increase). PDL calculation: PDL=Ln(final/initial cell number)/Ln(2);
The population doubling time (PDT), also called generation time, is the time needed for one population doubling. PDT calculation: PDT=Δt*Ln(2)/Ln(final/initial cell number).

Example 3

Production of Flaviviridae 3.1 Production of Yellow Fever Virus (YFV).

YFV amplification capacities of *Cairina moschata* immortalized avian cell lines ECACC 08060502 and 08060501 were evaluated and compared to VERO cell line which is the reference for Flaviridae propagation. *Cairina moschata* cell lines are grown in Basal Medium Eagle (Invitrogen) supplemented with 10% Foetal Calf Serum (FCS) and 4 mM L-Glutamine and the VERO cell line in Dulbecco's Modified Eagle's Medium (Invitrogen) supplemented with 5% FCS. Infections were performed in the same culture media. The Yellow fever 17D vaccine strain (YFV 17D) (Stamaril™, Sanofi Pasteur) was evaluated in this experiment. *Cairina moschata* immortalized avian cell lines ECACC 08060502 and 08060501 and VERO were seeded at respectively $4.10^5$, $2.10^5$ and $6.10^5$ cells in 6 well plates and cultivated for 24 hours in humid atmosphere at 37° C., 5% $CO_2$. The medium was then removed and cells infected at MOI 0.0001 with 250 μL YFV 17D virus diluted in culture medium. After a 1 hour absorption step, remaining virus suspension was removed, cells washed thrice with PBS and 2 mL medium were added to each well. Virus was recovered from supernatants after 24, 48 and 72 hours infection at 37° C., 5% $CO_2$, and clarified for titration. The infected cell layers were dissociated with trypsin, washed and fixed on slides. Indirect immunofluorescence analysis was performed on the slides in order to determine percentage of infected cells.

Titrations were performed by immunohistochemical assay on VERO cells infected with logarithmic virus dilutions. Five days after infection, cells were fixed, incubated with specific polyclonal IA (Immune Ascite), and revealed with a secondary antibody labelled with peroxidase. Colorimetric reaction was obtained using DAB substrate. Stained foci of infection were observed and counted, and viral titers were calculated as focus forming units (FFU) per ml.

Figure 7A:
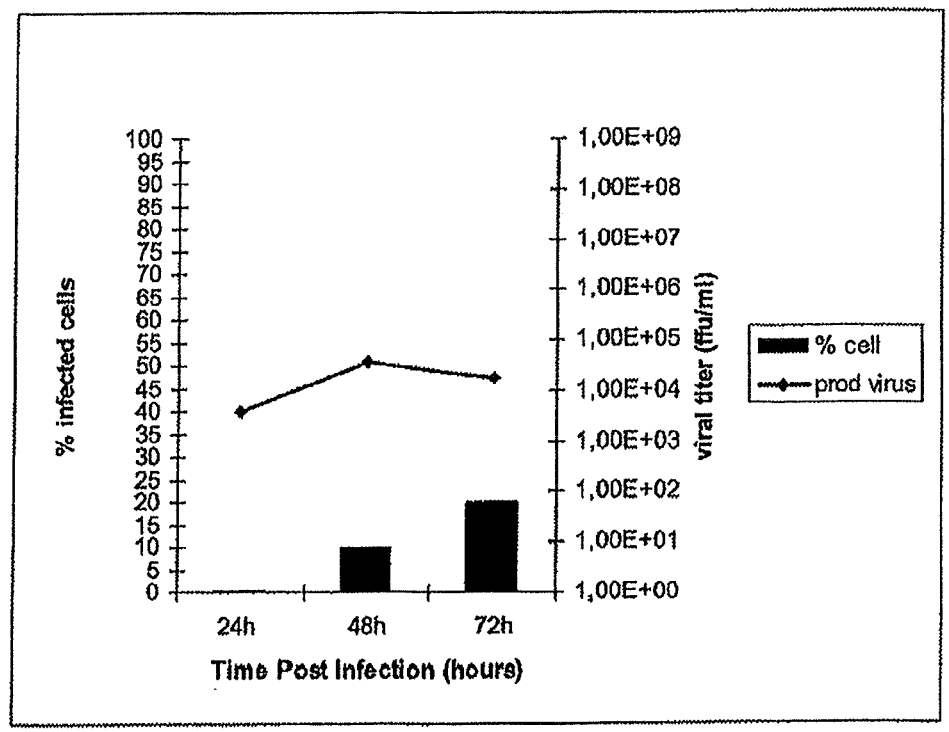
FIG. 7 (A-B) depicts the Flaviviridae production profile (Yellow Fever Virus 17D (Mol 0.001)) of *Cairina moschata* immortalized avian cell line ECACC 08060502 (FIG. 7A) and of VERO cell line (FIG. 7B).
Figure 7B:
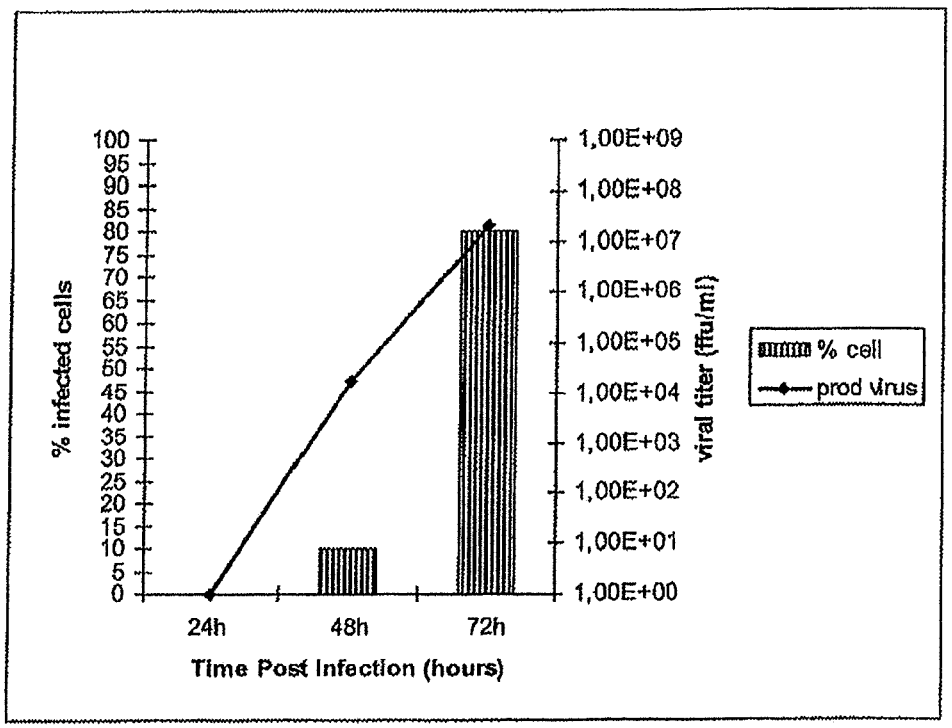
Figure 9A:
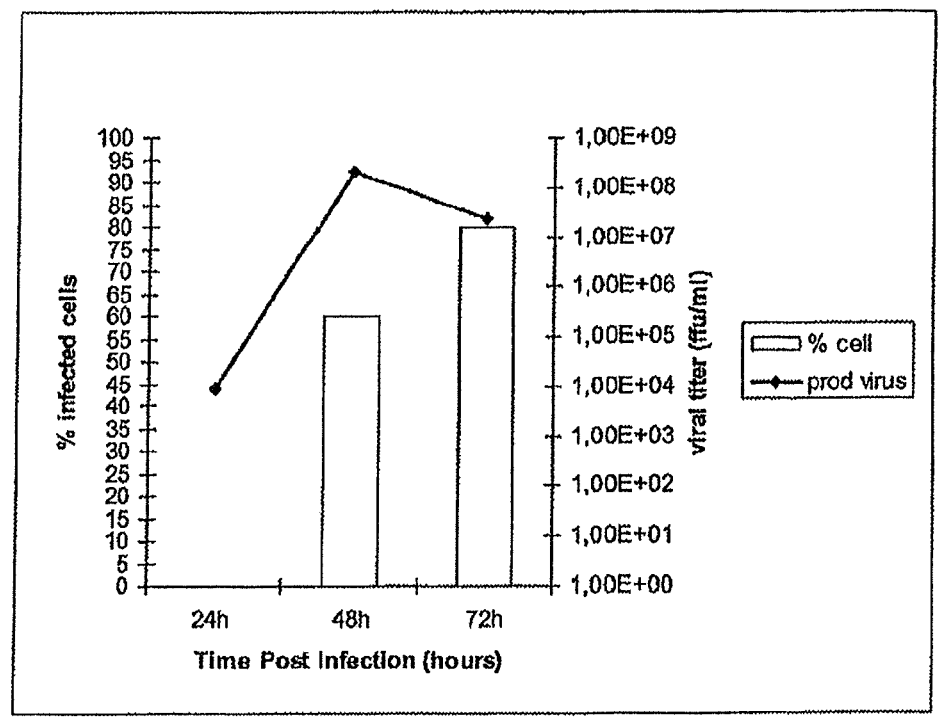
FIG. 9 (A-B) depicts the Flaviviridae production profile (Yellow Fever Virus 17D (Mol 0.001)) of the *Cairina moschata* immortalized avian cell line ECACC 08060501 (FIG. 9A) and of VERO cell line (FIG. 9B).
Figure 9B:
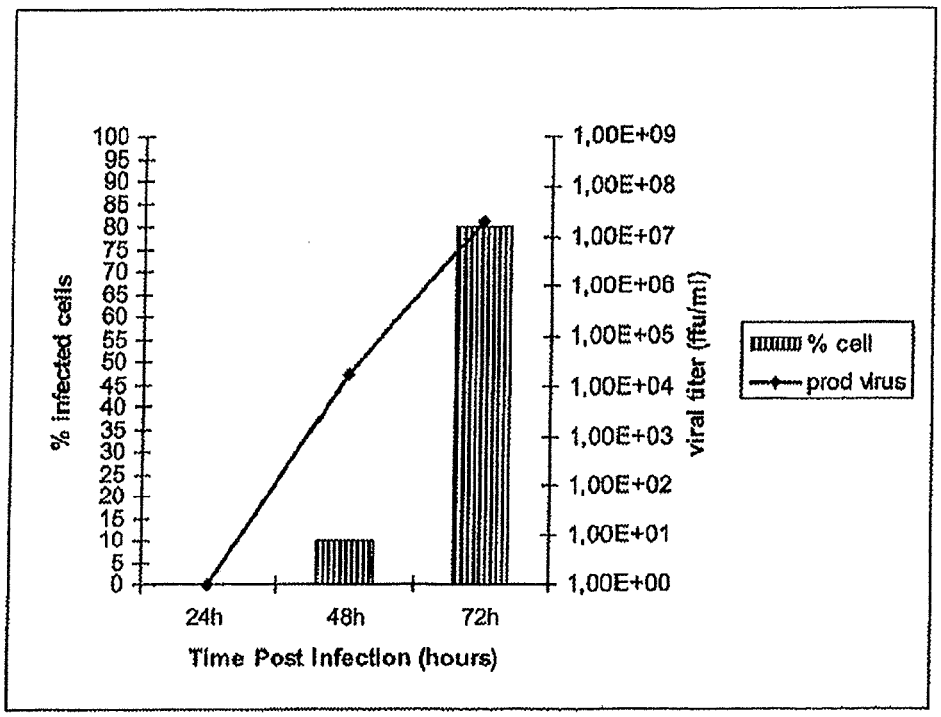

Results: As depicted in FIG. 7 (A-B), the viral titer obtained for YFV 17D with *Cairina moschata* immortalized avian cell line ECACC 08060502 (FIG. 7A) after only 24 hours is more than 3 log higher compared with the viral titer obtained with VERO cell line (FIG. 7B). As depicted in FIG. 9 (A-B), the viral titer obtained for YFV 17D with *Cairina moschata* immortalized avian cell line ECACC 08060501 (FIG. 9A) after only 24 and 48 hours is 4 log higher compared with the viral titer obtained with VERO cell line (FIG. 9B).

3.2 Production of Japanese Encephalitis Virus (JEV).

JEV amplification capacities of *Cairina moschata* immortalized avian cell lines ECACC 08060502 and 08060501 were evaluated and compared to VERO cell line which is the reference for Flaviridae propagation. *Cairina moschata* cell lines are grown in Basal Medium Eagle (Invitrogen) supplemented with 10% Foetal Calf Serum (FCS) and 4 mM L-Glutamine and the VERO cell line in Dulbecco's Modified Eagle's Medium (Invitrogen) supplemented with 5% FCS. Infections were performed in the same culture media. The Japanese Encephalitis Nakayama wild strain (collection of Centre National de la Recherche Scientifique (CNRS)) was evaluated in this experiment. *Cairina moschata* immortalized avian cell lines ECACC 08060502 and 08060501 and VERO were seeded at respectively $4.10^5$, $2.10^5$ and $6.10^5$ cells in 6 well plates and cultivated for 24 hours in humid atmosphere at 37° C., 5% $CO_2$. The medium was then removed and cells infected at MOI 0.0001 with 250 μL JEV Nakayama wild strain diluted in culture medium. After a 1 hour absorption step, remaining virus suspension was removed, cells washed thrice with PBS and 2 mL medium were added to each well. Virus was recovered from supernatants after 24, 48 and 72 hours infection at 37° C., 5% $CO_2$, and clarified for titration. The infected cell layers were dissociated with trypsin, washed and fixed on slides. Indirect immunofluorescence analysis was performed on the slides in order to determine percentage of infected cells.

Titrations were performed by immunohistochemical assay on VERO cells infected with logarithmic virus dilutions. Five days after infection, cells were fixed, incubated with specific polyclonal IA (Immune Ascite), and revealed with a secondary antibody labelled with peroxidase. Colorimetric reaction was obtained using DAB substrate. Stained foci of infection were observed and counted, and viral titers calculated as focus forming units (FFU) per ml.

Figure 8A:
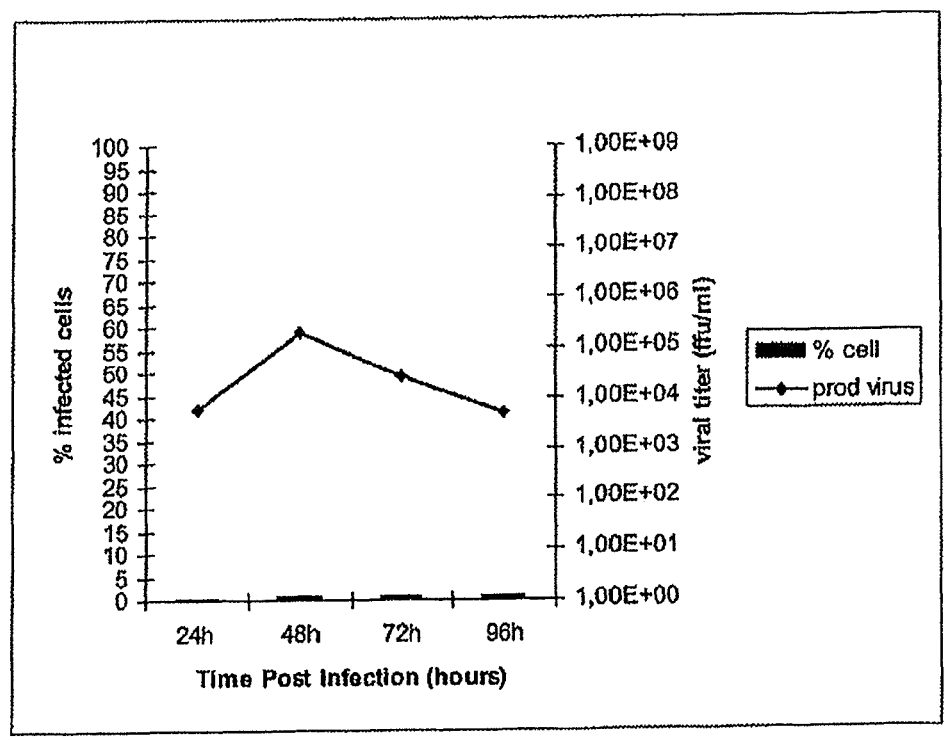
FIG. 8 (A-B) depicts the Flaviviridae production profile (Japanese Encephalitis Virus Nakayama wild strain (Mol 0.001)) of *Cairina moschata* immortalized avian cell line ECACC 08060502 (FIG. 8A) and of VERO cell line (FIG. 8B).
Figure 8B:
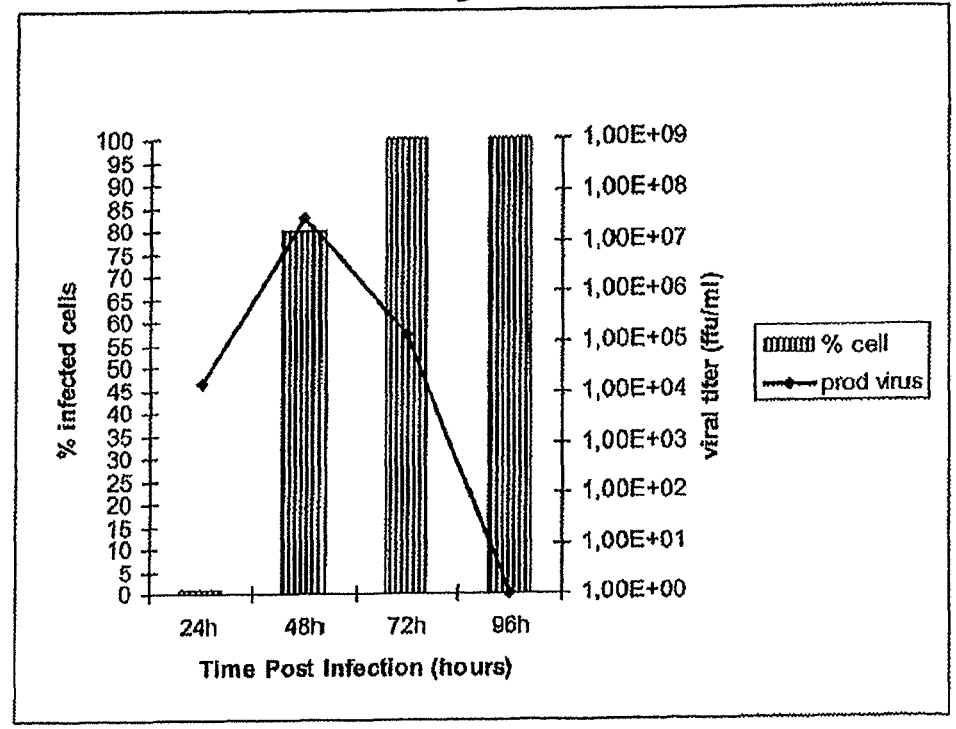
Figure 10A:
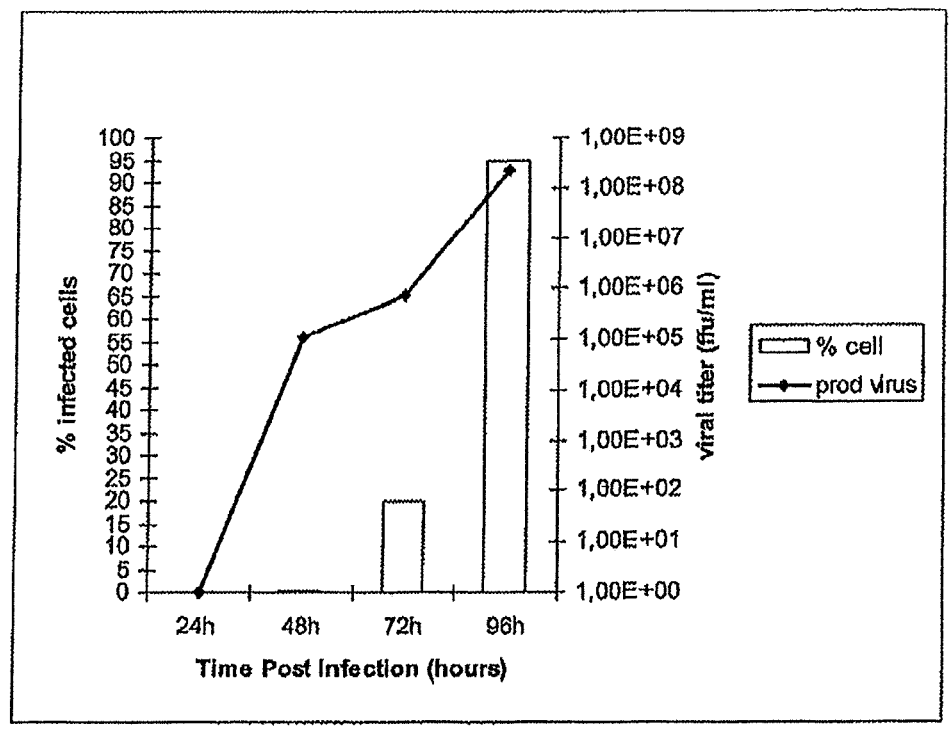
FIG. 10 (A-B) depicts the Flaviviridae production profile (Japanese Encephalitis Virus Nakayama wild strain (Mol 0.001)) of the *Cairina moschata* immortalized avian cell line ECACC 08060501 (FIG. 10A) and of the VERO cell line (FIG. 10B).
Figure 10B:
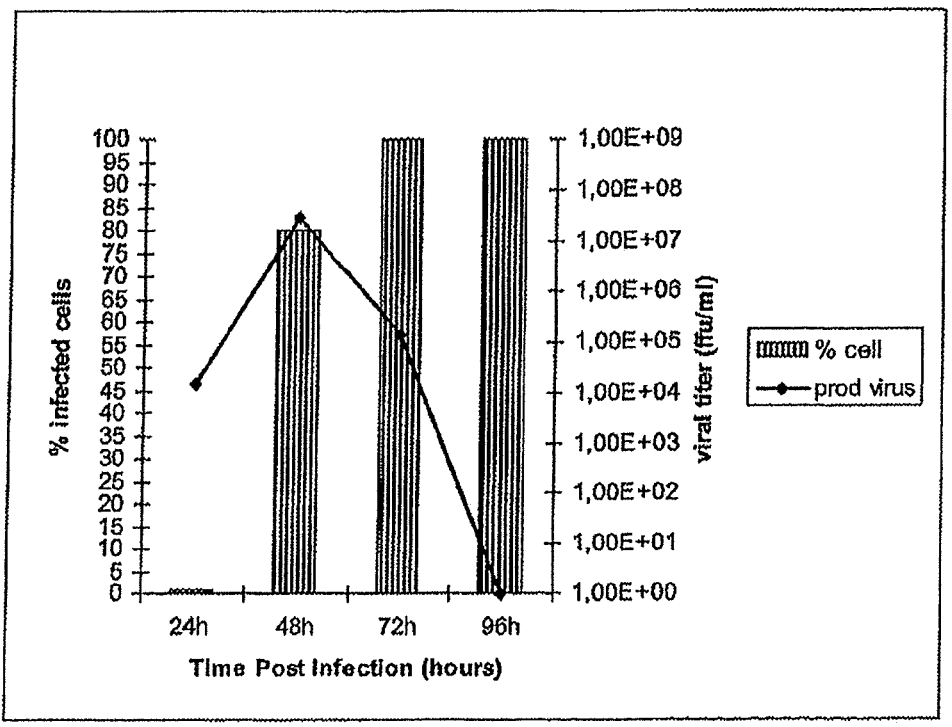

Results: As depicted in FIG. 8 (A-B), the viral titer obtained for JEV Nakayama wild strain with *Cairina moschata* immortalized avian cell line ECACC 08060502 (FIG. 8A) after 96 hours is more than 3 log higher compared with the viral titer obtained with VERO cell line (FIG. 8B). As depicted in FIG. 10 (A-B), the viral titer obtained for JEV Nakayama wild strain with *Cairina moschata* immortalized avian cell line ECACC 08060501 (FIG. 10A) after 72 and 96 hours is respectively 1 log and 8 log higher compared with the viral titer obtained with VERO cell line (FIG. 10B).

Example 4

Production of Poxviridae 4.1 Production of Modified Vaccinia Virus Ankara (MVA).

MVA amplification capacities of *Cairina moschata* immortalized avian cell lines ECACC 08060502 and 08060501 were evaluated and compared to primary chicken embryo fibroblasts (CEFs) usually used as substrate for MVA production. An MVA (Collection Nationale de Cultures de Microorganismes (CNCM) under depositary $N^{602}$ I-721) expressing eGFP was chosen in order to facilitate virus propagation follow up and titration. *Cairina moschata* immortalized avian cell lines ECACC 08060502 and 08060501 and CEFs were seeded at $2.10^6$ cells in T-flask of 25 cm² and cultivated for 24 hours in humid atmosphere at 37° C., 5% $CO_2$. The medium (Basal Medium Eagle (BME) supplemented with 10% Foetal Calf Serum (FCS) and 4 mM L-Glutamine) was then removed and cells infected at MOI 0.05 with 500 µL MVA virus diluted in PBS 1% cations, 1% FCS. After a 30 minutes adsorption step, remaining virus suspension was removed, cells washed once with PBS and 5 mL BME 10% FCS were then added to each flask. Virus was recovered by a freezing-thawing step from cells and supernatant after 0, 24, 48, 72 and 96 hours infection at 37° C., 5% $CO_2$. Recovered virus suspensions were sonicated prior to titration in order to avoid aggregates.

Titrations were performed in triplicates on CEFs seeded in 6 cm culture dishes, infected with logarithmic virus dilutions and overlaid with agar. Plaque forming units of MVA, expressing eGFP, were visualized with fluorescent binocular and counted after 72 hours. The *Cairina moschata* immortalized avian cell line ECACC 08060502 did not amplify MVA.

Figure 11A:
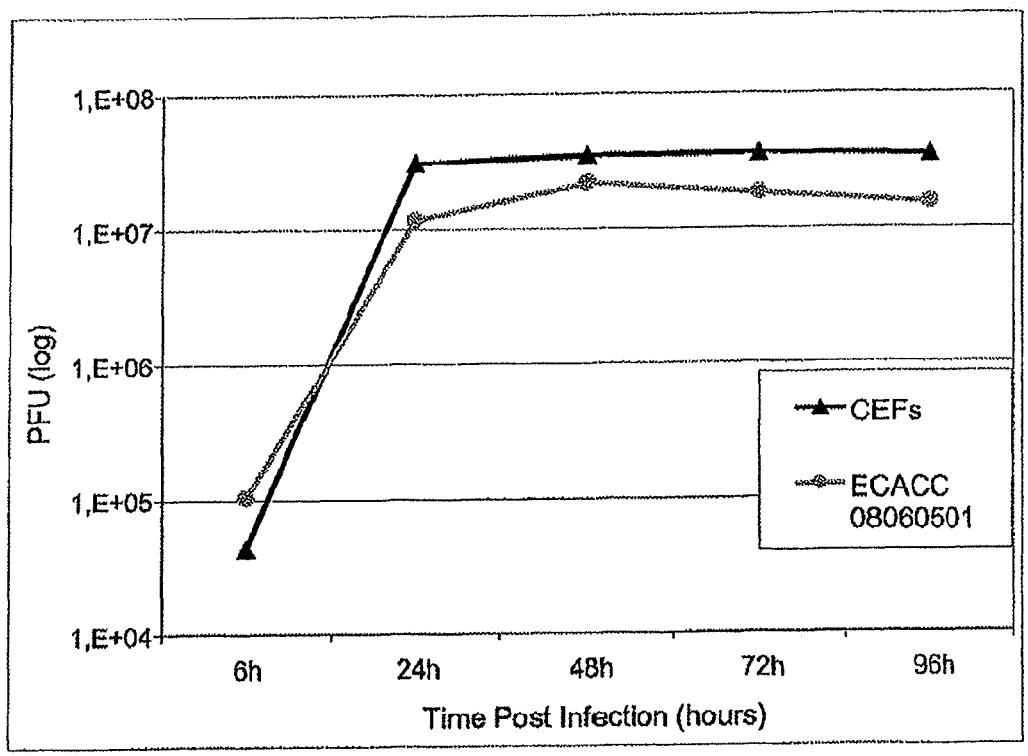
FIG. 11 (A-B) depicts the Poxviridae production profile (Vaccinia Virus strain Copenhagen (VV-COP) (FIG. 11B) and Modified Vaccinia virus Ankara (MVA) (FIG. 11A)) of the *Cairina moschata* immortalized avian cell line ECACC 08060501.

Results: As depicted in FIG. 11A, the *Cairina moschata* immortalized avian cell line ECACC 08060501 enables MVA amplification comparable to the one obtained with classical CEF substrate. The highest virus titers were reached for both *Cairina moschata* immortalized avian cell line ECACC 08060501 and CEFs after 48 h infection. Concordantly, clear cytopathic effect was observed in both cells (data not shown).

4.2 Production of Vaccinia Virus Strain Copenhagen (VV-COP).

VV-COP amplification capacities of *Cairina moschata* immortalized avian cell lines ECACC 08060502 and 08060501 were evaluated and compared to primary chicken embryo fibroblasts (CEFs) usually used as substrate for VV-COP production. A VV-COP strain (GOEBEL et al. 1990; Genbank accession number M35027.1) comprising a defective J2R gene (see WEIR and MOSS 1983; Genbank accession number AAA48082) was used for this experiment. *Cairina moschata* immortalized avian cell lines ECACC 08060502 and 08060501 and CEFs were seeded at $14.10^6$ cells in T-flask of 175 cm² and cultivated for 24 hours in humid atmosphere at 37° C., 5% $CO_2$. The medium (Basal Medium Eagle (BME) supplemented with 10% Foetal Calf Serum (FCS) and 4 mM L-Glutamine) was then removed and cells infected at MOI 0.0001 with 5 mL VV-COP virus diluted in PBS 1% cations, 1% FCS. After a 30 minutes adsorption step, 35 mL BME 10% FCS were added to each flask. Virus was recovered by a freezing-thawing step from cells and supernatant after 24, 48, 72 and 96 hours infection at 37° C., 5% $CO_2$. Recovered virus suspensions were sonicated prior to titration in order to avoid aggregates.

Titrations were performed in triplicates on BHK21 cells seeded in 6 well plates. Cells were infected with logarithmic virus dilutions and liquid culture media was added after 1 hour virus absorption. 24 hours later, media was removed and the cells overlaid with a mixture of crystal violet and red neutral. After staining of the cells, plaque forming units of virus were visualized with binocular and counted. The *Cairina moschata* immortalized avian cell line ECACC 08060502 did not amplify VV-COP.

Figure 11B:
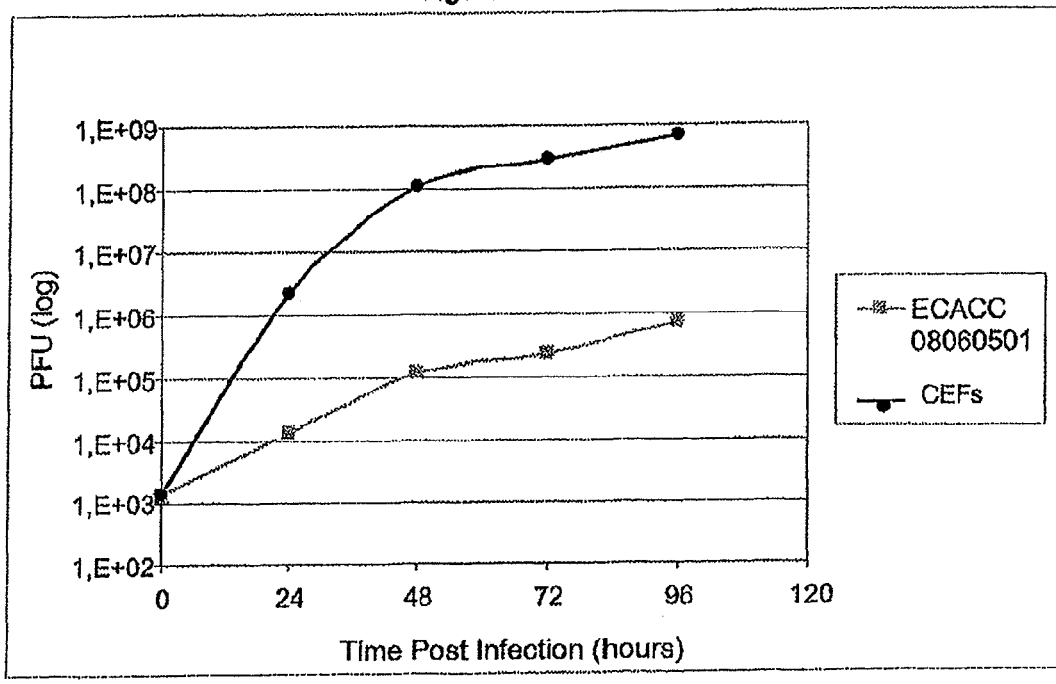

Results: As depicted in FIG. 11B, the *Cairina moschata* immortalized avian cell line ECACC 08060501 enables VV-COP amplification even if less efficient compared to the amplification obtained with classical CEF substrate.

Example 5

Production of IL-2

Supernatants from *Cairina moschata* immortalized avian cell lines ECACC 08060502 and 08060501 were transiently transfected with an IL-2 (CMV promoter) expression plasmid (pTG8363: human IL2 cloned in pCiNeo plasmid, CMV promoter). Supernatants were collected after 24, 48, 72 and 96 hours. IL-2 was quantified by ELISA (Quantikine, RD Systems) and functionality determined in a CTLL assay.

Results: Both cell lines ECACC 08060502 and 08060501 produced functional IL-2. Amount was equivalent between both cell lines. Furthermore level of production was independent from the transfection method used, ranging from 4865 IU/mL (CTLL) and 211 ng/mL (ELISA) corresponding to a specific activity of 23.1 IU/ng, to 5672 IU/mL (CTLL) and 308 ng/mL corresponding to a specific activity of 18.4 IU/ng. So the measured specific activities of IL-2 produced in the cells lines are at least equivalent to the 13.16 IU/ng WHO international standard for IL-2 (Human, Jurkat-derived).

Example 6

Production of Rituxan

Figure 12C:
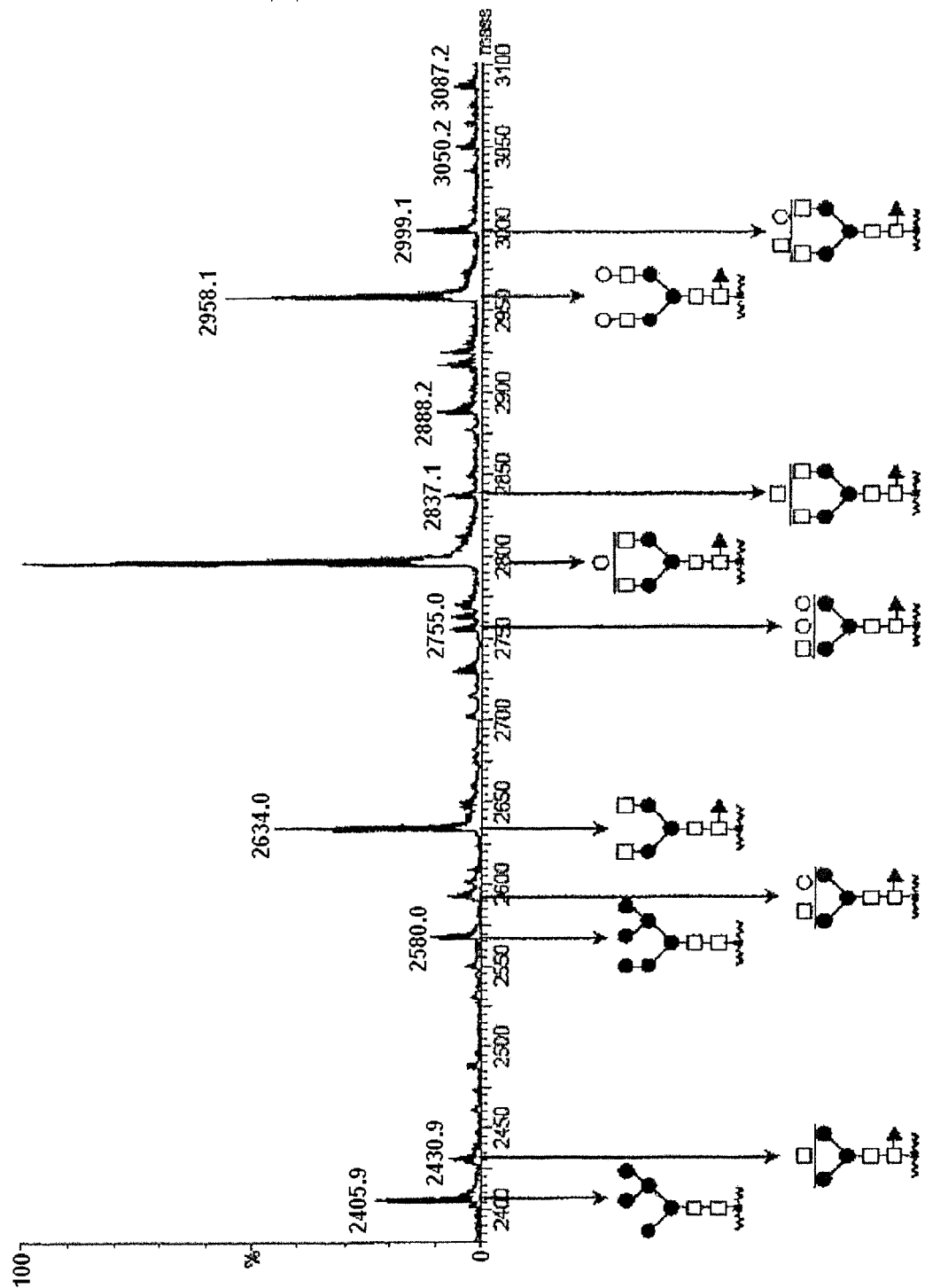
FIG. 12 (A-C) depicts the production of rituximab from *Cairina moschata* immortalized avian cell line ECACC 08060501 (FIG. 12C) and from CHO K1 cell line (FIG. 12A) and from CHO DG44 cell line (FIG. 12B).

Heavy and light chains were synthesized by GeneArt and corresponding expression plasmid assembled based on the pCI-Neo vector (Promega). Transient gene expression was performed with specific <<low IgG FCS>>. The *Cairina moschata* immortalized avian cell lines ECACC 08060502 and 08060501 were expanded 5 days in 10% low IgG FCS versus classic FCS. No negative effect on cell growth was observed. Supernatants from cell lines ECACC 08060502 and 08060501 were collected and the amount of monoclonal antibody was evaluated using an IgG ELISA (total human IgG, Bethyl). Results: In transient and non-optimized conditions up to 0.5 µg/per ml were produced in cell line ECACC 08060502 and up to 2.5 µg/per ml in cell line ECACC 08060501. Rituxan transiently produced either in CHO standard cell lines (CHO K1 (FIG. 12A) and CHO DG44 (FIG. 12B) a dihydrofolate reductase-deficient CHO clone) or in cell line ECACC 08060501 (FIG. 12C) was purified in order to analyze and compare the corresponding glycosylation patterns. Mass spectrometry analysis (FIG. 12 (A-C)) showed no fucosylation difference between CHO expressed Rituxan and cell line ECACC 08060501 expressed Rituxan.

Example 7

Production of Erythropoietin (EPO)

Expression transient assays were performed using a commercially available plasmid obtained from Invitrogen (GeneStorm® Human Clones, ref HK1000 RG001720, Invitrogen) and in which the human EPO was under control of a pCMV promoter.

Three transfection reagents were evaluated, in accordance with the manufacturer's instructions: Lipofectamine2000 (Invitrogen), Superfect (Qiagen) and Fugene6 (Roche); as well an electroporation device (Nucleofector, Basic Fibroblast kit, Amaxa). Supernatant from *Cairina moschata* immortalized avian cell lines ECACC 08060502 and 08060501 were collected after 48, 72 and 96 hours, and human EPO quantified by ELISA.

Figure 13:
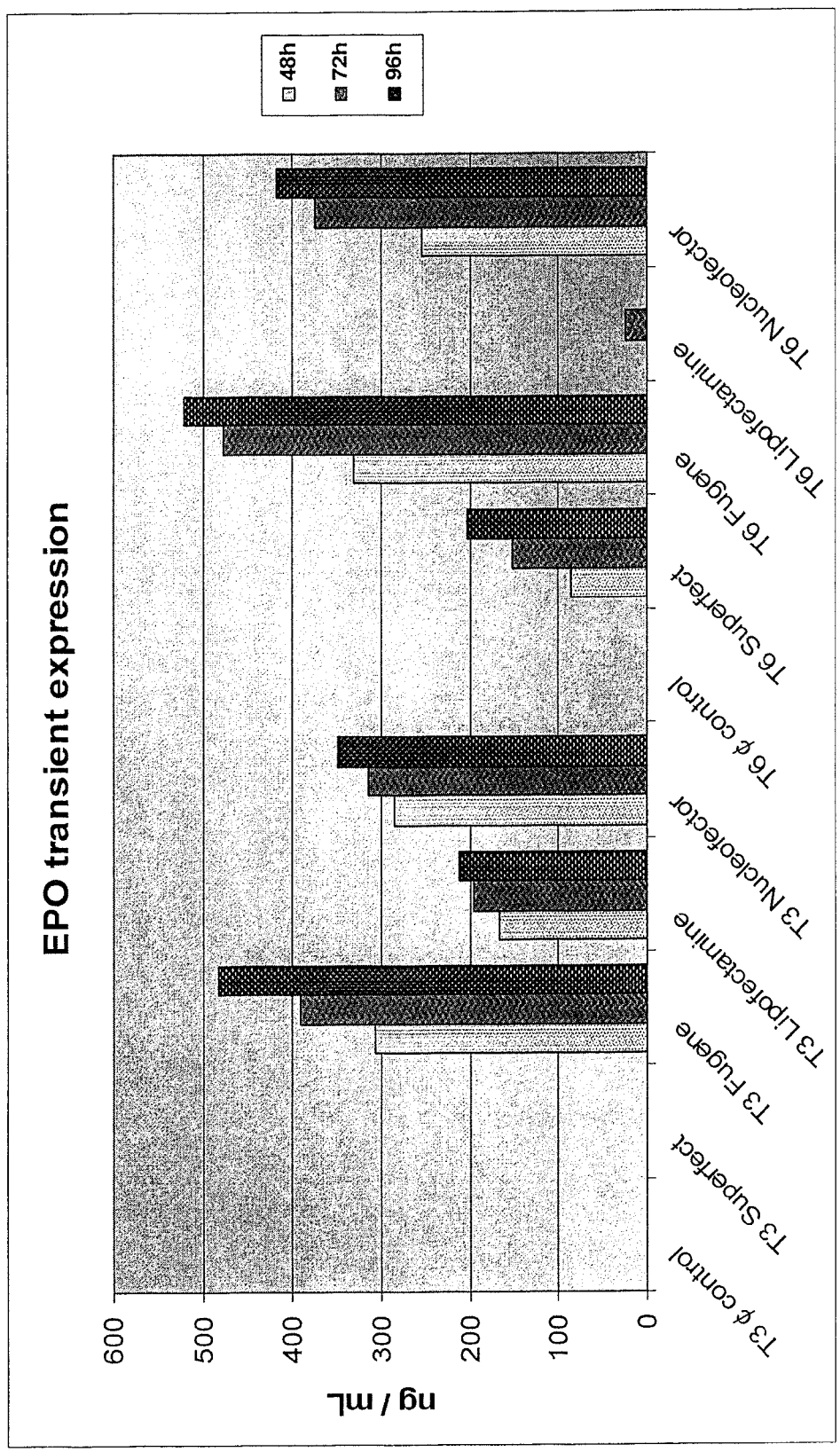
FIG. 13 depicts the production of erythropoietin (EPO) from *Cairina moschata* immortalized avian cell line ECACC 08060502 (T3) and ECACC 08060501 (T6).

Results: In both cell lines, maximum expression level was obtained after 96 hours using the Fugene6 transfection reagent followed by the Nucleofector System (FIG. 13). In transient and non-optimized conditions up to 0.5 µg/per ml were produced. All documents (e.g. patents, patent applications, publications) cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A method of making virus or protein using the immortalized avian cell line deposited at the European Collection of Cell Cultures (ECACC) under accession number 08060502 or 08060501.

2. The method of claim 1, wherein the protein is selected from the group consisting of antibodies, receptor ligands, hormones, cytokines, growth factors, cell adhesion molecules, blood clotting factors, enzymes, fragments thereof, and combinations thereof.

3. The method of claim 1, wherein the protein is selected from the group consisting of cytokines, antibodies, and hormones.

4. The method of claim 1, wherein the protein is selected from the group consisting of IL-2, rituximab, and erythropoietin (EPO).

5. A method of making a protein comprising the steps of:
    a) contacting the immortalized avian cell line deposited at the European Collection of Cell Cultures (ECACC) under accession number 08060502 or 08060501 with a recombinant vector comprising a nucleotide sequence encoding a protein; and
    b) culturing the cell line under conditions that allow the protein to be produced.

6. The method of claim 5, wherein the protein is selected from the group consisting of antibodies, receptor ligands, hormones, cytokines, growth factors, cell adhesion molecules, blood clotting factors, enzymes, fragments thereof, and combinations thereof.

7. The method of claim 5, wherein the protein is selected from the group consisting of cytokines, antibodies, and hormones.

8. The method of claim 5, wherein the protein is selected from the group consisting of IL-2, rituximab, and erythropoietin (EPO).

* * * * *